(12) United States Patent
Sano et al.

(10) Patent No.: US 10,588,591 B2
(45) Date of Patent: Mar. 17, 2020

(54) X-RAY IMAGING APPARATUS AND METHOD OF COMPOSING X-RAY IMAGING IMAGES

(71) Applicant: Shimadzu Corporation, Kyoto (JP)

(72) Inventors: Satoshi Sano, Kyoto (JP); Taro Shirai, Kyoto (JP); Takahiro Doki, Kyoto (JP); Akira Horiba, Kyoto (JP); Naoki Morimoto, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 161 days.

(21) Appl. No.: 16/002,495

(22) Filed: Jun. 7, 2018

(65) Prior Publication Data
US 2018/0368799 A1 Dec. 27, 2018

(30) Foreign Application Priority Data
Jun. 22, 2017 (JP) .................................. 2017-122259

(51) Int. Cl.
*A61B 6/00* (2006.01)

(52) U.S. Cl.
CPC .......... *A61B 6/5235* (2013.01); *A61B 6/4035* (2013.01); *A61B 6/4291* (2013.01); *A61B 6/484* (2013.01); *A61B 6/5264* (2013.01)

(58) Field of Classification Search
CPC ................................................ G21K 2207/005
See application file for complete search history.

(56) References Cited

U.S. PATENT DOCUMENTS

| | | | |
|---|---|---|---|
| 2009/0074139 A1* | 3/2009 | Hempel ............. | A61B 5/14532 378/62 |
| 2018/0217071 A1* | 8/2018 | Chen ................... | G01N 23/046 |
| 2018/0261350 A1* | 9/2018 | Yun ........................ | G21K 1/025 |
| 2019/0310208 A1* | 10/2019 | Sharma ................ | G01N 23/046 |

FOREIGN PATENT DOCUMENTS

| | | |
|---|---|---|
| JP | 2011-206160 A | 10/2011 |
| JP | 2012-016370 A | 1/2012 |

OTHER PUBLICATIONS

Extended European Search Report dated Nov. 14, 2018 in the corresponding European patent application No. 18175122.3.

* cited by examiner

*Primary Examiner* — Yara B Green
(74) *Attorney, Agent, or Firm* — Muir Patent Law, PLLC

(57) ABSTRACT

The X-ray imaging apparatus is equipped with an image processing unit for performing a position adjustment of a first dark field image and a second dark field image based on a positional difference amount between a first absorption image of an object and a second absorption image of the object.

10 Claims, 17 Drawing Sheets

First Embodiment

First Embodiment

First Embodiment

View showing the object as viewed from the side

First Embodiment

First Embodiment

Second Embodiment

Second Embodiment

Second Embodiment

Object in second relative position and absorption image and dark field image to be generated Second Embodiment Second Embodiment Second Embodiment Second Embodiment Second Embodiment Second Embodiment Second Embodiment

First Modification of First Embodiment

X-RAY IMAGING APPARATUS AND METHOD OF COMPOSING X-RAY IMAGING IMAGES

CROSS-REFERENCE TO RELATED APPLICATIONS

The priority application number JP2017-122259, entitled "X-RAY IMAGING APPARATUS AND METHOD OF COMPOSING X-RAY IMAGING IMAGES" filed on Jun. 22, 2017, invented by Satoshi Sano, Taro Shirai, Takahiro Doki, Akira Horiba, and Naoki Morimoto, upon which this patent application is based is hereby incorporated by reference.

BACKGROUND OF THE INVENTION

Field of the Invention

The present invention relates to an X-ray imaging apparatus and a method of composing X-ray imaging images, more particularly to an X-ray imaging apparatus and a method of composing X-ray imaging images for generating an absorption image, a phase differential image, and a dark field image by a Talbot Lau interferometer.

Background Technique

Conventionally, an X-ray imaging apparatus for generating an absorption image, a phase differential image, and a dark field image by a Talbot Lau interferometer is known. Such an X-ray imaging apparatus is disclosed in, for example, Japanese Unexamined Patent Application Publication No. 2012-16370.

In Japanese Unexamined Patent Application Publication No. 2012-16370, an X-ray imaging apparatus is disclosed in which an absorption image, a phase differential image, and a dark field image are generated from nine images obtained by translating gratings at equal intervals by 1/9 period in the periodic direction.

Note that the "phase differential image" denotes an image obtained by imaging based on a phase displacement of an X-ray caused when the X-ray passes through an object. Further, the "dark field image" denotes a visibility image obtained by a change in visibility based on small-angle scattering of an object. Further, the dark field image is also called small-angle scattering image. The "visibility" denotes sharpness.

Here, in nondestructive inspections and/or medical applications, in some cases, it is desired to confirm the ultrastructure of an inside of an object. Generally, in an absorption image acquired by an X-ray imaging apparatus, it is difficult to confirm the ultrastructure of an inside of an object. However, according to the dark field image or the phase differential image disclosed in Japanese Unexamined Patent Application Publication No. 2012-16370, an internal structure of an object which could not be confirmed by an absorption image can be confirmed.

However, when capturing a dark field image or a phase differential image, in cases where there is directivity in X-ray diffusion due to an ultrastructure of an inside of an object, depending on the relation between the orientation of the grating pattern of the grating and the direction of the object (diffusion direction), there is an inconvenience that a component in one direction among X-ray diffusion directions due to the ultrastructure of the inside of the object is emphasized, which makes it difficult to image the entire ultrastructure in detail.

In this case, it is considered that it becomes possible to grasp the details of the ultrastructure of the inside of the object by composing a plurality of images captured while changing the relationship between the orientation of the grating pattern of the grating and the orientation of the object by performing the position adjustment, etc. However, when composing dark field images or phase differential images, when the orientation of the grating pattern of the grating is different from the direction of object, there is a problem that the shaped of the object in the obtained image differ and therefore the position adjustment cannot be performed.

The present invention has been made to solve the aforementioned problems, and an object of the present invention is to provide an X-ray imaging apparatus and a method of composing X-ray imaging images capable of performing a position adjustment of an image even when a shape of an object to be imaged differs depending on a positional relationship between an orientation of a grating pattern of a grating and an orientation of the object.

SUMMARY OF THE INVENTION

In order to attain the aforementioned object, an X-ray imaging apparatus according to one aspect of the present invention includes an X-ray source; a detector configured to detect an X-ray irradiated from the X-ray source; a plurality of gratings arranged between the X-ray source and the detector, the plurality of gratings including a first grating to which the X-ray is irradiated from the X-ray source and a second grating to which the X-ray that has passed through the first grating is irradiated; and an image processing unit configured to generate a first image including an absorption image and a second image including an image other than the absorption image captured in the same arrangement as the first image from an intensity distribution of the X-ray detected by the detector, wherein the image processing unit is configured to perform a position adjustment of the second image in the first relative position and the second image in the second relative position based on a positional difference amount of an object between the first image in the first relative position and the first image in the second relative position among images captured by arranging the plurality of gratings and the object in the first relative position and the second relative position in two mutually different axial directions.

In this specification, the "positional difference amount" denotes a coordinate difference of the object in the acquired image. Further, the "first relative position" and the "second relative position" denote a relative position in which an object and a plurality of gratings are arranged so that the positional relationship between the plurality of gratings and the object in the optical axis direction of the X-ray is the same and the orientation of the grating pattern of the gratings and the orientation of the object are different from each other.

Further, in the first relative position and the second relative position, in cases where an object is arranged in an inclined manner, the orientation of the rotation axis at the time of tilting the object in the respective relative position is the same direction. That is, in cases where the object is inclined in the first relative position and the second relative position, the object is inclined by performing the rotational movement in the same plane.

Here, in the absorption image, in the first relative position and the second relative position, the object shapes in the acquired images are the same without depending on the relationship between the orientation of the grating pattern of the gratings and the orientation of the object. Therefore, by configuring as described above, even if the object shapes of the acquired second images are different in the first relative position and the second relative position, the position adjustment of the second image can be performed based on the positional difference amount of the object of the first image in which the object shape is the same in the first relative position and the second relative position. As a result, the position adjustment of the image can be performed even in cases where the object shapes to be imaged differ depending on the positional relationship between the orientation of the grating pattern of the gratings and the orientation of the object.

In the X-ray imaging apparatus according to the aforementioned one aspect, it is preferably configured such that the image processing unit is configured to acquire a movement amount of the first image as the positional difference amount of the object by performing a position adjustment of the first image in the first relative position and the first image in the second relative position.

With this configuration, by adjusting the position of the first image in the first relative position and the second relative position, it is possible to easily acquire the movement amount of the first image as the positional difference amount of the object.

In the X-ray imaging apparatus according to the aforementioned one aspect, it is preferably configured such that the image processing unit is configured to perform the position adjustment of the first image by performing fitting from shape information of the object of the first image in the first relative position and the second relative position, acquire the movement amount of the first image at the time of the position adjustment by the fitting, and move the second image by the same amount as the acquired movement amount.

With this configuration, the position adjustment of the first image can be easily performed by performing the fitting based on the shape information of the first image. Also, by moving the second image by the same amount as the movement amount of the first image, it is possible to easily perform the position adjustment of the second image.

In this specification, the "shape information" denotes information on the shape of an object imaged in an image.

In the X-ray imaging apparatus according to the aforementioned one aspect, it is preferably configured such that the second image is either one of a dark field image and a phase differential image.

With this configuration, the position adjustment can be performed using the absorption image which does not change the shape of the object to be imaged depending on the relative position between the grating and the object. As a result, the position adjustment of at least one of the dark field image and the phase differential image in which the shape of object to be obtained sometimes differs depending on the relative position between the grating and the object can be easily performed.

In the X-ray imaging apparatus according to the aforementioned one aspect, it is preferably configured such that the first relative position is a relative position in which the plurality of gratings and the object are arranged such that the object faces in a predetermined direction with respect to the grating pattern of the plurality of gratings, and the second relative position is a relative position in which the plurality of gratings and the object are arranged such that an orientation of the object with respect to the grating pattern of the plurality of gratings differs from the first relative position.

With this configuration, it is possible to prevent the object and the grating pattern of the plurality of gratings from becoming the same orientation in the first relative position and the second relative position. As a result, it is possible to image in a state in which the X-ray diffusion direction by the ultrastructure of the inside of the object differs in the first relative position and the second relative position, so that the structure of the inside of the object can be grasped.

In the X-ray imaging apparatus according to the aforementioned one aspect, it is preferably configured to further include a rotation mechanism configured to relatively rotate either one of the object and an imaging system including the X-ray source, the detector, and the plurality of gratings in a rotational direction about an axis in a vertical direction orthogonal to an optical axis direction of the X-ray, wherein the first image and the second image each include a three-dimensional image.

With this configuration, it becomes possible to use a three-dimensional image of the absorption image as a first image, and by performing the position adjustment of the three-dimensional image of the absorption image, the position adjustment of the three-dimensional image of the dark field image and/or the phase differentiation can be easily performed as a second image. As a result, it becomes possible to grasp in detail the X-ray diffusion direction in the ultrastructure of the inside of the object. That is, it is possible to acquire an image reflecting the difference in the microscopic structure of the ultrastructure of the inside of the object or the difference in the shape of the fine structure of the inside of the object.

In this case, it is preferable that the image processing unit is configured to generate the first image and the second image from images captured while rotating the object or the imaging system in each of a third relative position, a fourth relative position, a fifth relative position, and a sixth relative position, which are arranged so that the orientation of the object with respect to the grating pattern of the plurality of gratings differs, in addition to the first relative position and the second relative position, in each of six mutually different axial directions.

With this configuration, for example, it is possible to distinguish the difference in the diffusion direction of 45 degrees, 135 degrees, etc. As a result, it is possible to grasp the ultrastructure of the inside of the object in more detail. That is, by capturing images in the first to sixth relative positions, it is possible to grasp an arbitrary diffusion direction of the ultrastructure of the inside of the object.

In the X-ray imaging apparatus according to the aforementioned one aspect, it is preferably configured such that the image processing unit is configured to compose the second image in the first relative position and the second image in the second relative position and display regions different in a diffusion direction of the X-ray in a composite image.

With this configuration, it is possible to distinguishably display regions different in the X-ray diffusion directions. As a result, it is possible to grasp the internal structure of the dark field image and/or the phase differential image in more detail.

In the X-ray imaging apparatus according to the aforementioned one aspect, it is preferably configured such that the image processing unit is configured to perform the position adjustment of the first image based on an X-ray high absorbency marker provided on the object.

With this configuration, even in cases where there is no directivity in the shape of the object such as a sphere, the position adjustment of the first image can be easily performed based on the X-ray high absorbency marker.

In the composition method of the X-ray imaging image in the second aspect of the present invention, a method of composing an X-ray imaging image, includes: a step of capturing a first image including an absorption image and a second image including an image other than the absorption image with a plurality of gratings and an object arranged in a first relative position and a second relative position in two mutually different axial directions; a step of acquiring a movement amount from the first image in the first relative position to the first image in the second relative position; and a step of performing a position adjustment of the second image based on the movement amount of the first image.

With this, even if the object shapes of the acquired second image are different in the first relative position and the second relative position, the position adjustment of the second image can be performed based on the positional difference amount of the object T of the first image in which the shape of the object T is the same in the first relative position and the second relative position. As a result, the position adjustment of the image can be performed even in cases where the shape of the object to be imaged differs depending on the positional relationship between the orientation of the grating pattern of the gratings and the orientation of the object.

DESCRIPTION OF PREFERRED EMBODIMENTS

Hereinafter, embodiments of the present invention will be described with reference to the drawings.

First Embodiment

With reference to FIGS. 1 to 5, a configuration of an X-ray imaging apparatus 100 according to a first embodiment of the present invention and a method of composing X-ray imaging images will be described.

Configuration of X-Ray Imaging Apparatus

First, the configuration of the X-ray imaging apparatus 100 according to the first embodiment will be described with reference to FIGS. 1 to 4.

Figure 1:
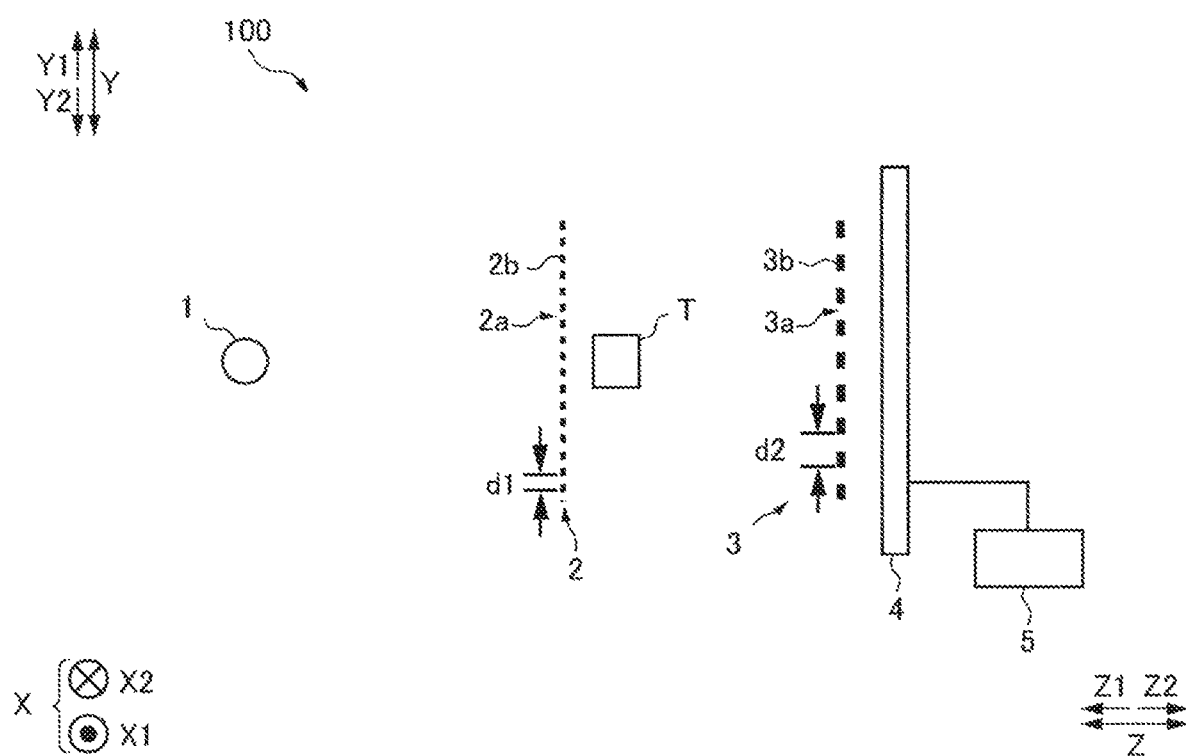
FIG. 1 is a diagram showing an overall structure of an X-ray imaging apparatus according to a first embodiment of the present invention.

As shown in FIG. 1, the X-ray imaging apparatus 100 is an apparatus for imaging an inside of an object T by utilizing diffusion of the X-ray that has passed through the object T. Further, the X-ray imaging apparatus 100 is an apparatus for imaging the inside of the object T using a Talbot effect. For example, in nondestructive inspection applications, the X-ray imaging apparatus 100 can be used for imaging the inside of the object T as an object. Further, for example, in medical applications, the X-ray imaging apparatus 100 can be used for imaging the inside of the object T as a living body.

FIG. 1 is a view showing the X-ray imaging apparatus 100 as viewed from the side. As shown in FIG. 1, the X-ray imaging apparatus 100 is equipped with an X-ray source 1, a first grating 2, a second grating 3, a detector 4, and an image processing unit 5.

In this specification, the direction from the X-ray source 1 to the first grating 2 is denoted as a Z2-direction, and the opposite direction thereof is denoted as a Z1-direction. The left-right direction in a plane orthogonal to the Z-direction is denoted as an X-direction, the direction toward the rear side of the paper surface is denoted as an X2-direction, and the direction toward the front side of the paper surface denoted as an X1-direction. Further, the vertical direction in the plane orthogonal to the Z-direction denoted as a Y-direction, the upward direction is denoted as a Y1-direction, and the downward direction is denoted as a Y2-direction. Note that the Y-direction is an example of the "vertical direction orthogonal to the optical axis direction of the X-ray" recited in claims. The Z-direction is an example of the "optical axis direction of the X-ray" recited in claims.

The X-ray source 1 is configured to generate an X-ray by being applied by a high voltage and irradiate the generated X-ray in the Z2-direction.

The first grating 2 is provided with a plurality of slits 2a and X-ray phase change portions 2b arranged in the Y-direction at a predetermined period (pitch) d1. The slit 2a and X-ray phase change portion 2b are each formed so as to extend linearly. The first grating 2 is a so-called phase grating.

The first grating 2 is arranged between the X-ray source 1 and the second grating 3 and configured to be irradiated by the X-ray from the X-ray source 1. The first grating 2 is provided to form a self-image (not shown) of the first grating 2 by a Talbot effect. When an X-ray with coherence passes through a grating in which slits are formed, a grating image (self-image) is formed at a position away from the grating by a predetermined distance (Talbot distance). This is called a Talbot effect.

The second grating 3 includes a plurality of X-ray transmission portions 3a and X-ray absorption portions 3b arranged at a predetermined period (pitch) d2 in the Y-direction. The X-ray transmission portion 3a and the X-ray absorption portion 3b are each formed so as to extend linearly. The second grating 3 is a so-called absorption grating. The first grating 2 and the second grating 3 are gratings having different roles, respectively, but the slit 2a and the X-ray transmission portion 3a each transmit the X-ray. Further, the X-ray absorption portion 3b plays a role of shielding the X-ray, and the X-ray phase change portion 2b changes the phase of the X-ray by the difference in the refractive index with the slit 2a.

The second grating 3 is arranged between the first grating 2 and the detector 4, and is irradiated by the X-ray that has passed through the first grating 2. Further, the second grating 3 is arranged at a position away from the first grating 2 by the Talbot distance. The second grating 3 interferes with the self-image of the first grating 2 to form a moire fringe (not shown) on the detection surface of the detector 4.

The detector 4 is configured to detect an X-ray, convert the detected X-ray into an electric signal, and read the converted electric signal as an image signal. The detector 4 is, for example, an FPD (Flat Panel Detector). The detector 4 is composed of a plurality of conversion elements (not shown) and a plurality of pixel electrodes (not shown) arranged on the plurality of conversion elements. A plurality of conversion elements and pixel electrodes are arrayed in the X-direction and the Y-direction at a predetermined period (pixel pitch). Further, the detector 4 is configured to output the acquired image signal to the image processing unit 5.

The image processing unit 5 is configured to generate an absorption image, a dark field image, and a phase differential image based on the image signal output from the detector 4. The image processing unit 5 includes, for example, a CPU (Central Processing Unit) and a GPU (Graphics Processing Unit).

In the first embodiment, the method of capturing the image of the object T is not particularly limited, and the image of the object may be acquired by any method as long as it is a method capable of acquiring the absorption image, the dark field image, and the phase differential image of the object T, such as, e.g., a fringe scanning method and a moire fringe image method. The fringe scanning method is a method in which image capturing is performed while translating the first grating 2 or the second grating 3 at a predetermined pitch, an intensity-modulated signal is created based on the X-ray intensity detected for each pixel, and imaging is performed based on the created intensity modulation signal. Further, the method by a moire fringe image is a method of imaging the object T by detecting the scattering of the X-ray by the object T based on the moire fringe appearing when the object T is arranged.

Next, with reference to FIGS. 2 to 5, the configuration will be described in which the image processing unit 5 performs the position adjustment of the absorption image, the position adjustment of the dark field image based on the movement amount of the absorption image at the time of the position adjustment is performed, and the dark field image is composed.

Figure 2A:
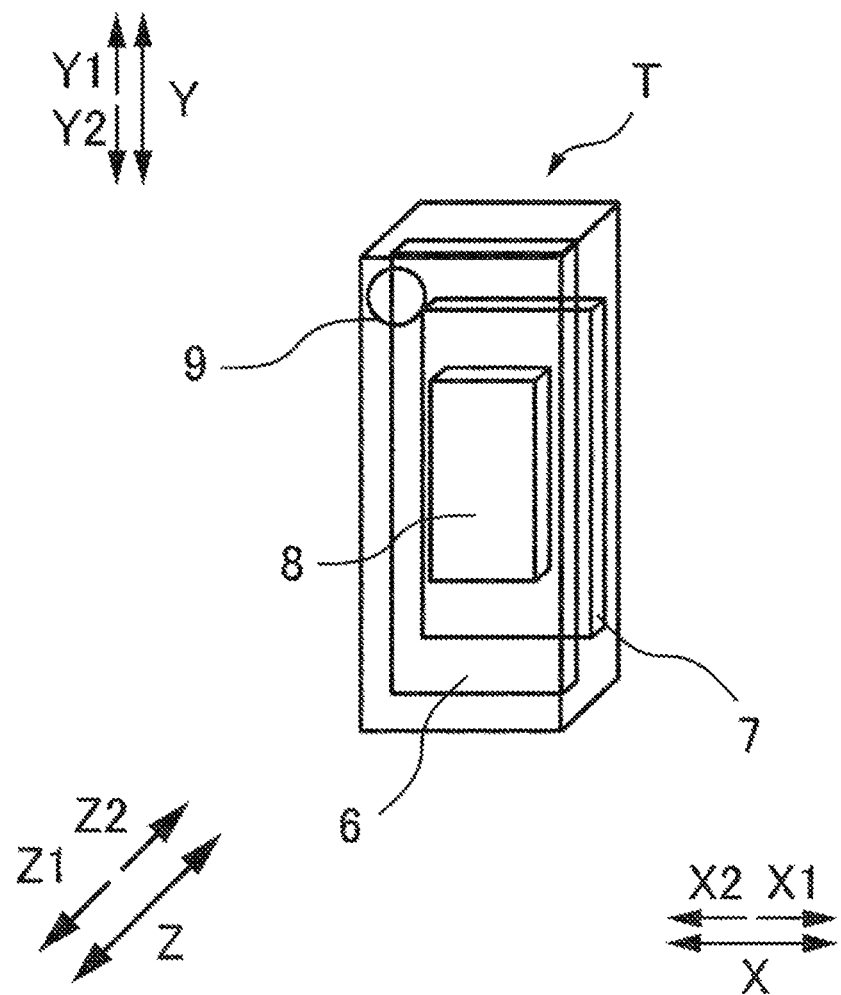
FIG. 2A is a schematic perspective view of an object as viewed from the Z1-direction.
Figure 2B:
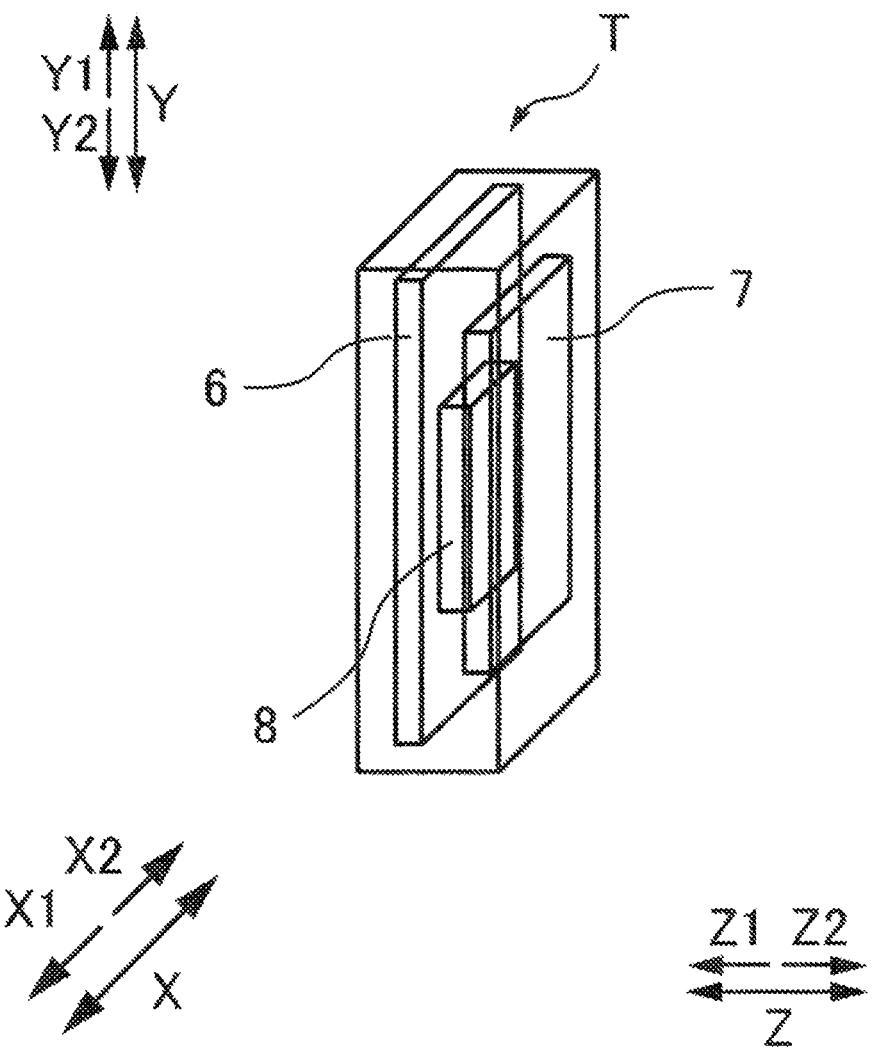
FIG. 2B is a schematic perspective view of the object as viewed from the X1-direction.

FIG. 2 is a diagram showing the internal structure of the object T. In the example shown in FIG. 2, when the object T is arranged so that the longitudinal direction thereof is oriented in the Y-direction, the object T includes therein a first scatterer 6 strong in X-ray diffusion in the vertical direction (Y-direction), a second scatterer 7 strong in X-ray diffusion in the lateral direction (X-direction), and a third scatterer 8 strong in X-ray diffusion in the oblique direction (oblique direction in the plane defined by the X-direction and the Y-direction). The object T, the first scatterer 6, the second scatterer 7, and the third scatterer 8 each have the same X-ray attenuation coefficient. That is, the object T, the first scatterer 6, the second scatterer 7, and the third scatterer 8 have the same X-ray absorption.

Also, as shown in FIG. 2A, an X-ray high absorbency marker 9 is provided on the object T. The marker 9 is composed of heavy metal having high X-ray absorbency. Metal having high X-ray absorbency, such as, e.g., gold and lead, is used for the marker 9. Further, as shown in FIG. 2, in the first embodiment, an object T having a rectangular parallelepiped shape is used.

Here, in cases where there exists a scatterer having an ultrastructure that diffuses an X-ray in the object T, there occur a number of boundaries in the object T by each ultrastructure. An X-ray is diffused by multiple refractions at a number of boundaries. As a result, the coherence of the X-ray after transmitting through the object is attenuated, which can visualize the existence of the scatterer as a dark field image. In the case of using a Talbot Lau interferometer, there is a characteristic that the diffusion component in the vertical direction (array direction of slits) is particularly high in sensitivity with respect to the orientation of the grating pattern of the grating.

Note that the orientation of the grating pattern of the grating denotes a direction in which the X-ray transmission portion, the slit, the X-ray absorption portion, and the X-ray phase change portion of each grating extends. Moreover, in the case of using a Talbot Lau interferometer, the diffusion component in the horizontal direction (the direction in which the slit extends) with respect to the grating pattern of the grating has no change in the intensity of the X-ray detected by the diffusion due to the internal structure of the object T. Therefore, there is a property that it is hard to be imaged.

Figure 3:
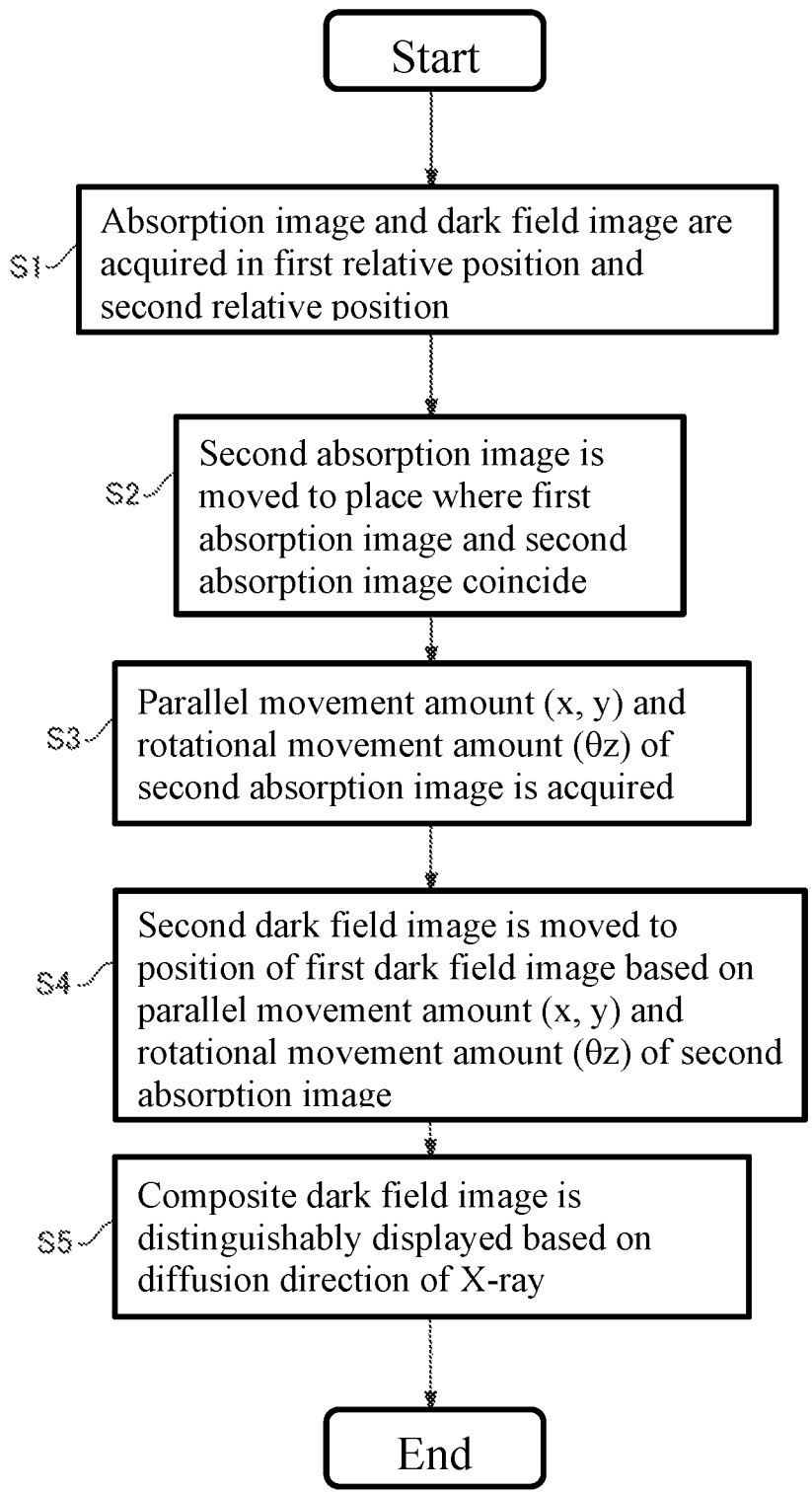
FIG. 3 is a flowchart for explaining a method of composing images by the X-ray imaging apparatus according to the first embodiment of the present invention.

Next, with reference to FIG. 2 and FIG. 3, an overall flow of the configuration in which the X-ray imaging apparatus 100 according to the first embodiment performs the position adjustment of the dark field image to generate a composite dark field image will be described.

In Step S1, the X-ray imaging apparatus 100 captures a first absorption image 10 (see FIG. 4A), a first dark field image 11 (see FIG. 4A), a second absorption image 12 (see FIG. 4B), and a second dark field image 13 (see FIG. 4B) by arranging a plurality of gratings and the object T in the first relative position and the second relative position in different two axial directions. That is, as shown in FIG. 2A, the X-ray imaging apparatus 100 captures the first absorption image 10 and the first dark field image 11 in the first relative position in which the object T is arranged with the longitudinal direction of the object T oriented in the Y-direction.

Further, the X-ray imaging apparatus 100 captures the second absorption image 12 and the second dark field image 13 in the second relative position (see FIG. 4B) in which the object T is arranged with the longitudinal direction of the object T oriented in the X-direction.

The "two mutually different axial directions" denote two mutually different directions in a plane defined by the X-direction and the Y-direction. Further, in the first embodiment, in order to maintain the magnitude of the object T to be imaged constant, the X-ray imaging apparatus 100 performs image capturing without changing the positional relationship of the X-ray source 1, the plurality of gratings, the object T, and the detector 4 in the Z-direction. Further, in the first relative position and the second relative position, in order to make the imaging surface of the object T to be imaged the same, the rotational movement of the object T is only a rotational movement in the rotational direction ($\theta z$ direction) about the axis in the Z-direction. Further, considering the orientation of the grating pattern, at least the second relative position is preferably a position obtained by rotating the object T or the plural of gratings by 90 degrees about the Z-axis from the first relative position.

Figure 5:
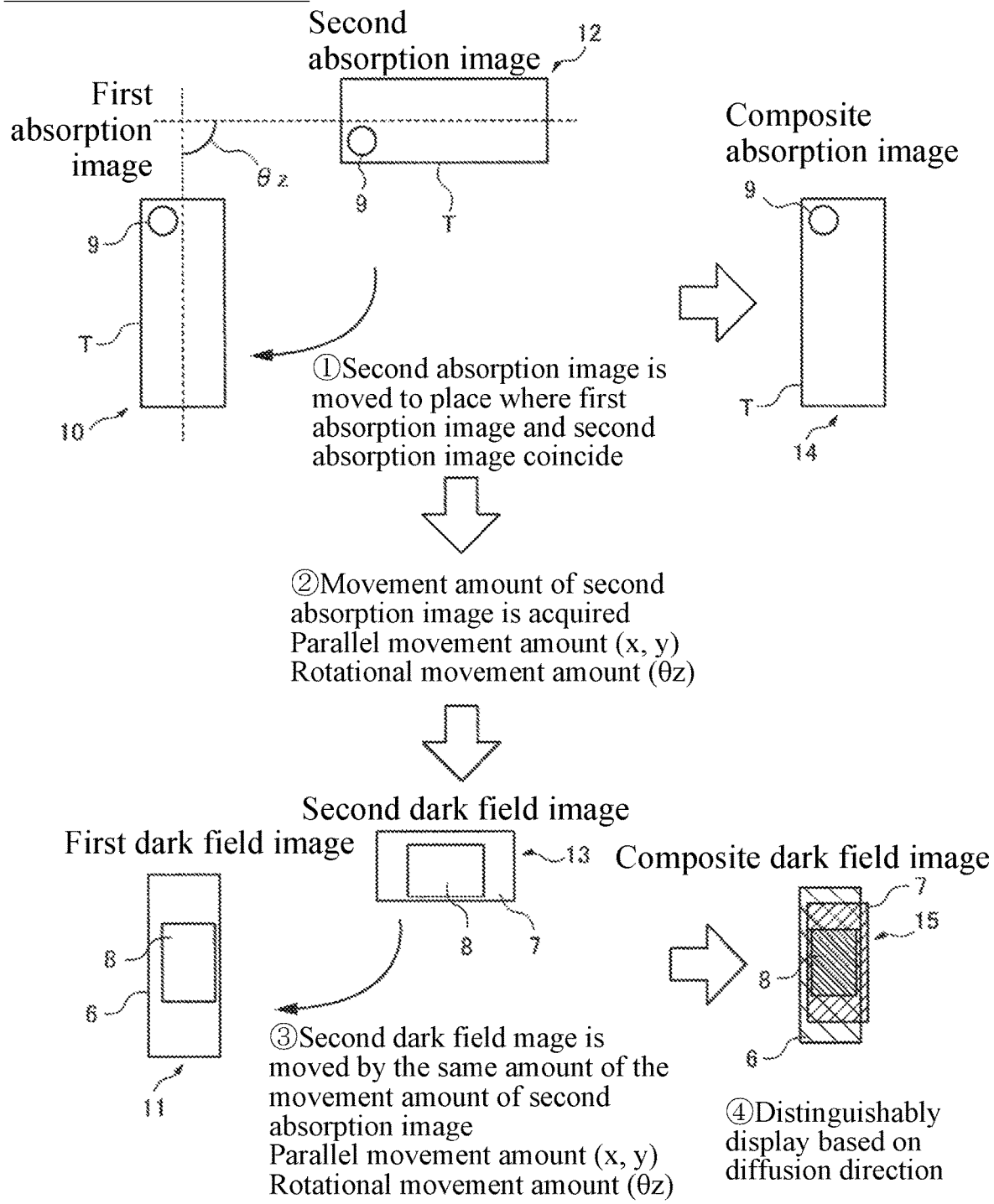
FIG. 5 is a schematic diagram for explaining a method of composing images by the X-ray imaging apparatus according to the first embodiment of the present invention.

Next, in Step S2, the image processing unit 5 performs the position adjustment between the first absorption image 10 in the first relative position and the second absorption image 12 in the second relative position and generates a composite absorption image 14 (see FIG. 5). As a method of the position adjustment, for example, a method in which the position is adjusted by fitting using the shape information of the first absorption image 10 in the first relative position and the second absorption image 12 in the second relative position is used.

It should be noted that the first absorption image 10 and the second absorption image 12 are each an example of the "first image" recited in claims. Further, the first dark field image 11 and the second dark field image 13 are each an example of the "second image" recited in claims.

Next, in Step S3, the image processing unit 5 acquires the movement amount of the second absorption image 12. The movement amounts to be acquired are a parallel movement amount (x, y) and a rotational movement amount ($\theta z$). The parallel movement amount (x, y) and the rotational movement amount ($\theta z$) are each an example of the "positional difference amount" recited in claims.

Next, in Step S4, based on the movement amounts (the parallel movement amount (x, y) and the rotational movement amount ($\theta z$)) of the second absorption image 12 acquired in Step S3, the image processing unit 5 performs the position adjustment of the first dark field image 11 and the second dark field image 13 and generates a composite dark field image 15 (see FIG. 5). Note that the composite dark field image 15 is an example of the "composite image" recited in claims.

Next, in Step S5, the image processing unit 5 distinguishably displays regions different in the X-ray diffusion direction in the composite dark field image 15.

As described above, the X-ray imaging apparatus 100 according to the first embodiment is configured to perform the position adjustment of the first dark field image 11 and the second dark field image 13 by acquiring the movement amount of the second absorption image 12 from the first absorption image 10 and the second absorption image 12 in which the shape of the object T does not change in the first relative position and the second relative position and then moving the second dark field image 13 by the same amount as the movement amount of the second absorption image 12.

Next, with reference to FIG. 4 and FIG. 5, the configuration in which the X-ray imaging apparatus 100 in the first embodiment generates the composite dark field image 15 will be described.

Figure 4A:
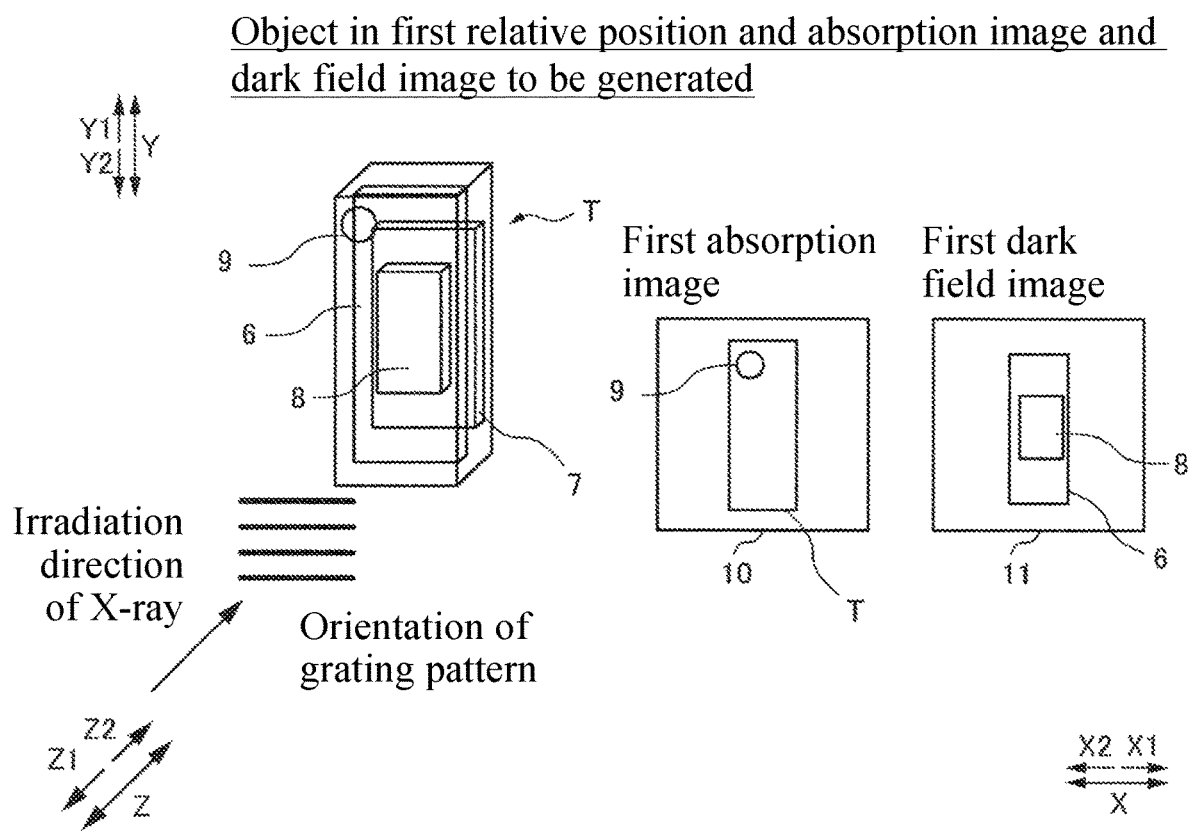
FIG. 4A is a schematic diagram for explaining a first relative position and an image to be captured in the first relative position according to the first embodiment of the present invention.
Figure 4B:
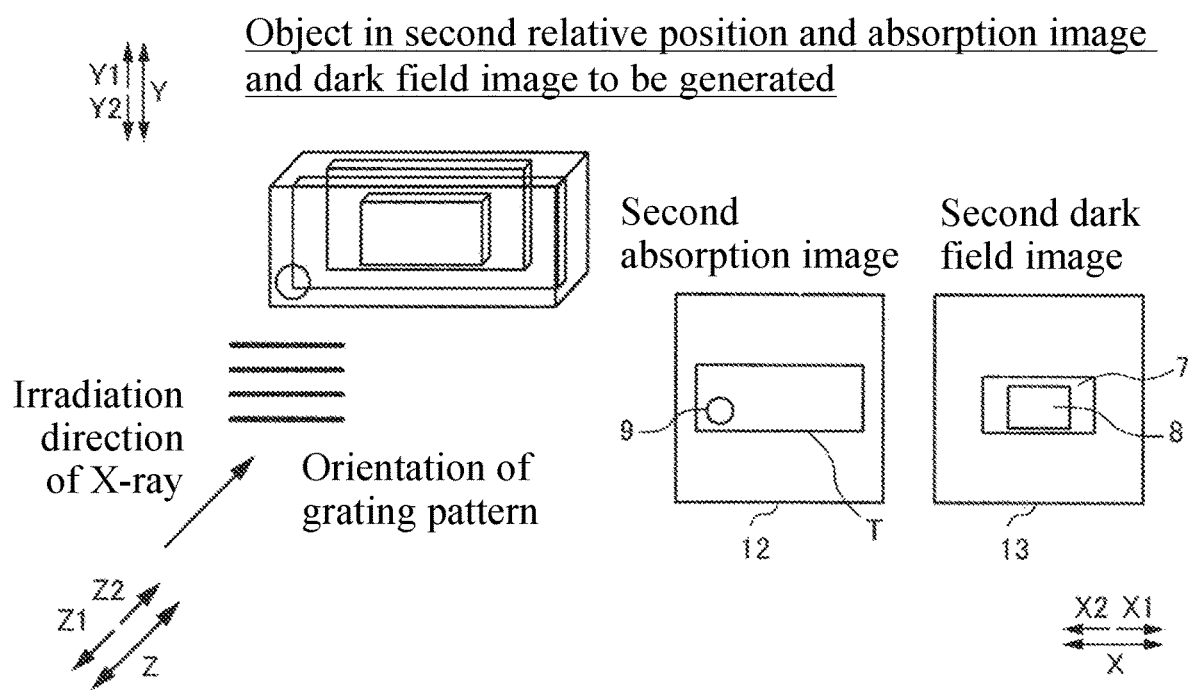
FIG. 4B is a schematic diagram for explaining a second relative position and an image to be captured in the second relative position according to the first embodiment of the present invention.

FIG. 4A is a diagram showing a first relative position in which the longitudinal direction of the object T is oriented in the Y-direction. FIG. 4B is a diagram showing a second relative position in which the transverse direction of the object T is oriented in the Y-direction. In the example shown in FIG. 4A, the first relative position is a relative position in which a plurality of gratings and the object T are arranged so that the longitudinal direction of the object T becomes a predetermined direction (orthogonal direction) with respect to the grating pattern of the plurality of gratings.

In the example shown in FIG. 4B, the second relative position is a relative position in which a plurality of gratings and the object T are arranged so that the orientation of the longitudinal direction of the object T with respect to the grating pattern of the plurality of gratings (the orientation of the longitudinal direction of the object T becomes parallel to the grating pattern) is different from that in the first relative position. Further, as shown in FIG. 4, the grating is arranged so that the orientation of the grating pattern faces in the X-direction in each of the first relative position and the second relative position. In the first embodiment, the movement of the object T is limited to the rotational movement in the rotational direction about the X-direction, the Y-direction, and the Z-direction.

In the first embodiment, as shown in FIG. 4A, in the first relative position, the image processing unit 5 generates a first absorption image 10 and a first dark field image 11 captured in the same arrangement as the first absorption image 10 from the X-ray intensity distribution detected by the detector 4. Further, as shown in FIG. 4B, in the second relative position, the image processing unit 5 generates a second absorption image 12 and a second dark field image 13 captured in the same arrangement as the second absorption image 12 from the X-ray intensity distribution detected by the detector 4.

As shown in FIG. 4, although the first absorption image 10 captured in the first relative position and the second absorption image 12 captured in the second relative position are different in the orientation of the object T and the position in the image, the shape of the object T is the same. However, the first dark field image 11 captured in the first relative position and the second dark field image 13 captured in the second relative position are different in all of the orientation of the object T, the position in the image, and the shape.

Specifically, in the first relative position, the object T is arranged with the longitudinal direction of the object T oriented in the Y-direction. Therefore, in the first dark field image 11, the longitudinal direction is oriented in the Y-direction, and the first scatterer 6 and the third scatterer 8 are imaged. On the other hand, in the second relative position, since the object T is arranged with the longitudinal direction of the object T oriented in the X-direction, the longitudinal direction of the second dark field image is oriented in the X-direction and the second scatterer 7 and the third scatterer 8 are imaged.

Here, in the case of composing the first absorption image 10 and the second absorption image 12, and in the case of composing the first dark field image 11 and the second dark field image 13, the position adjustment of the image is required in respective cases.

In the first relative position and the second relative position, in cases where accurate movement information of the object T can be acquired, the position adjustment can be performed based on the movement information of the object T. However, in cases where the movement information of the object T cannot be obtained in the first relative position and the second relative position, or in cases where the accuracy of the acquired movement information cannot be secured, as described above, it can be considered to perform the position adjustment by fitting from the shape.

The first absorption image 10 and the second absorption image 12 are the same in the shape of the object T, and therefore the position adjustment can be performed by fitting by the shape. However, as shown in FIG. 4, the first dark field image 11 and the second dark field image 13 are different with each other in the shape of the imaged object T, and therefore the position adjustment cannot be performed by fitting by the shape.

Here, in the first embodiment, since the first absorption image 10 and the first dark field image 11 can be acquired simultaneously and therefore there is no change in arrangement and they exist in the same coordinate system. Therefore, the coordinate of the object T in the first absorption image 10 and that in the first dark field image 11 coincide with each other. Further, in the second absorption image 12 and the second dark field image 13, the coordinate of the object T in each image coincides. That is, the positional difference amount between the first absorption image 10 and the second absorption image 12 is the same as the positional difference amount between the first dark field image 11 and the second dark field image 13.

Therefore, in the first embodiment, as shown in FIG. 5, the image processing unit 5 is configured to perform the position adjustment of the first dark field image 11 in the first relative position and the second dark field image in the second relative position based on the positional difference amount of the object T between the first absorption image 10 in the first relative position and the second absorption image 12 in the second relative position among the images captured by arranging a plurality of gratings and the object T in the first relative position and the second relative position in the two mutually different axial directions.

Specifically, as shown in FIG. 5, the image processing unit 5 is configured to acquire the movement amount of the second absorption image as the positional difference amount of the object T by performing the position adjustment of the first absorption image 10 in the first relative position and the second absorption image 12 in the second relative position.

In the first embodiment, the image processing unit 5 is configured to perform the position adjustment of the second absorption image 12 by fitting from the shape information of the object T of the first absorption image 10 and the second absorption image 12 in the first relative position and the second relative position, acquire the parallel movement amount (x, y) and the rotational movement amount (θz) of the second absorption image 12 at the time of the position adjustment by fitting, and move the second dark field image 13 by the same amount as the acquired parallel movement amount (x, y) and rotational movement amount (θz).

At the time of the fitting, the image processing unit 5 performs the position adjustment of the second absorption image 12 based on the marker 9 provided in the object T. With this, for example, even in cases where the object T is of a shape with no directivity, such as, e.g., a spherical shape, the position adjustment can be performed by performing the fitting from the shape of the absorption image acquired by the marker 9.

Thereafter, the image processing unit 5 composes the first dark field image 11 in the first relative position and the second dark field image 13 in the second relative position to generate a composite dark field image 15. With this, it becomes possible to compose the first dark field image 11 in which the first scatterer 6 and the third scatterer 8 are imaged and the second dark field image 13 in which the second scatterer 7 and the third scatterer 8 are imaged, so that a composite dark field image 15 in which the first scatterer 6, the second scatterer 7, and the third scatterer 8 are reflected can be acquired.

Further, the image processing unit 5 is configured to distinguishably display regions different in the X-ray diffusion direction in the composite dark field image 15. In the composite dark field image 15, as a method of distinguishably displaying regions different in the X-ray diffusion direction, for example, there is a method of taking an arctangent of the ratio between the luminance value (pixel value) of the first dark field image 11 and the luminance value (pixel value) of the second dark field image 13 and performing the color display in accordance with the values.

The first dark field image 11 is an image based on the X-ray diffused in the X-direction, and the second dark field image 13 is an image based on the X-ray diffused in the Y-direction. Therefore, it is considered that the value obtained by taking the arctangent of the ratio between the luminance value (pixel value) of the first dark field image 11 and the luminance value (pixel value) of the second dark field image 13 is a value derived from the diffusion angle of the X-ray. Therefore, by performing the color display by the obtained values, it is possible to perform the display while distinguishing the X-ray diffusion direction by the ultra-structure of the inside of the object T. Further, by taking the difference between the luminance value (pixel value) of the first dark field image 11 and the luminance value (pixel value) of the second dark field image 13, the strength of the diffusion directivity can be displayed.

Effects of Structure of First Embodiment

In the first embodiment, the following effects can be obtained.

In the first embodiment, as described above, the X-ray imaging apparatus 100 is provided with the X-ray source 1, the detector 4, a plurality of gratings including the first grating 2 and the second grating 3, and an image processing unit 5 for generating a first absorption image 10, a first dark field image 11 imaged in the same arrangement as the first absorption image 10, a second absorption image 12, and a second dark field image 13 imaged in the same arrangement as the second absorption image 12. The image processing unit 5 is configured to perform the position adjustment of the first dark field image 11 in the first relative position and the second dark field image 13 in the second relative position based on the positional difference amount of the object T between the first absorption image 10 in the first relative position and the second absorption image 12 in the second relative position among the images captured by arranging a plurality of gratings and the object T in the first relative position and the second relative position in the two mutually different axial directions.

Here, in the absorption image, in the first relative position and the second relative position, the orientation of the rotation axis at the time of rotating the object T is the same. Therefore, the shape of the object T in the image to be obtained is the same without depending on the relationship between the orientation of the grating pattern of the grating and the orientation of the object T. Therefore, even in cases where the shape of the object T of the first dark field image 11 and that of the second dark field image 13 are different in the first relative position and the second relative position, the position adjustment of the second dark field image 13 can be performed based on the positional difference amount of the object T of the first absorption image 10 and the second absorption image 12 having the same shape of the object T in the first relative position and the second relative position. As a result, the position adjustment of the image can be performed even in cases where the shape of the object T imaged differs depending on the positional relationship between the orientation of the grating pattern of the grating and the orientation of the object T.

Further, in the first embodiment, as described above, the image processing unit 5 is configured to acquire the parallel movement amount (x, y) and the rotational movement amount (θz) of the second absorption image 12 as the positional difference amount of the object T by performing the position adjustment of the first absorption image 10 in the first relative position and the second absorption image 12 in the second relative position. As a result, by performing the position adjustment of the first absorption image 10 and the second absorption image 12 in the first relative position and the second relative position, the parallel movement amount (x, y) and the rotational movement amount (θz) of the second absorption image 12 as the positional difference amount of the object T can be easily acquired.

Further, in the first embodiment, as described above, the image processing unit 5 is configured to perform the position adjustment of the first absorption image 10 and the second absorption image 12 by fitting from the shape information of the first absorption image 10 and the second absorption image 12 in the first relative position and the second relative position, acquire the parallel movement amount (x, y) and the rotational movement amount (θz) of the second absorption image 12 at the time of the position adjustment by fitting, and move the second dark field image 13 by the same amount as the acquired parallel movement amount (x, y) and rotational movement amount (θz).

With this, by performing the fitting from the shape information of the first absorption image 10 and the second absorption image 12, the position adjustment of the first absorption image 10 and the second absorption image 12 can be easily performed. Further, by moving the second dark field image 13 by the same amount as the parallel movement amount (x, y) and rotational movement amount (θz) of the second absorption image 12, it is possible to easily perform the position adjustment of the first dark field image 11 and the second dark field image 13.

Further, in the first embodiment, as described above, the second image is a dark field image. With this, the position adjustment can be performed using the first absorption image 10 and the second absorption image 12 in which the shape of the object T imaged is not changed depending on the relative position of the grating and the object T. As a result, it is possible to easily perform the position adjustment of the second dark field image 13 and the second dark field image 13 in which the shape of object T obtained sometimes differs depending on the relative position of the grating and the object T.

In the first embodiment, as described above, the first relative position is a relative position in which a plurality of gratings and the object T are arranged so that the object T is oriented in a predetermined direction (orthogonal direction) with respect to the grating pattern of a plurality of gratings, while the second relative position is a relative position in which a plurality of gratings and the object T are arranged so that the orientation of the object T with respect to the grating pattern of a plurality of gratings differs from that in the first relative position.

This makes it possible to prevent the object T and the grating pattern of the plurality of gratings from having the same orientation in the first relative position and the second relative position. As a result, it is possible to image in a state in which the X-ray diffusion direction by the ultrastructure of the inside of the object T differs in the first relative position and the second relative position, so that the structure of the inside of the object T can be grasped.

Composition Method of X-Ray Imaging Image

Next, with reference to FIGS. 4 and 5, the method of composing X-ray imaging images in the first embodiment will be described.

First, with reference to FIG. 4, steps of capturing a first absorption image 10 and a second absorption image 12, and a first dark field image 11 and a second dark field image 13 by arranging a plurality of gratings and the object T in the first relative position and the second relative position in two mutually different axis directions will be described.

As shown in FIG. 4A, in the first relative position, the grating is arranged so that the orientation of the grating pattern is oriented in the X-direction. In the first relative position, the object T is arranged so that the longitudinal direction of the object T is oriented in the Y-direction. Further, as shown in FIG. 4B, in the second relative position, the grating is arranged so that the orientation of the grating pattern is oriented in the X-direction. Further, in the second relative position, the object T is arranged so that the longitudinal direction of the object T is oriented in the X-direction.

In the first embodiment, as shown in FIG. 4, in the first relative position, a first absorption image 10 and a first dark field image 11 imaged in the same arrangement as the first absorption image 10 are captured. Further, in the second embodiment, a second absorption image 12 and a second dark field image 13 captured in the same arrangement as the second absorption image 12 are captured.

Next, with reference to FIG. 5, a step of acquiring the first absorption image 10 in the first relative position and the movement amount of the second absorption image 12 in the second relative position and a step of performing the position adjustment of the first dark field image 11 and the second dark field image 13 based on the movement amount of the second absorption image 12 will be described.

In the first embodiment, as shown in FIG. 5, the second absorption image 12 is moved to a position where the first absorption image 10 and the second absorption image 12 coincides. At that time, the image processing unit 5 acquires the parallel movement amount (x, y) and the rotational movement amount (θz). Then, in the first embodiment, the position adjustment of the first dark field image 11 and the second dark field image 13 is performed based on the acquired parallel movement amount (x, y) and rotational movement amount (θz).

Effects of Image Composition Method of First Embodiment

In the first embodiment, the following effects can be obtained.

In the first embodiment, as described above, the method includes a step of capturing a first absorption image 10 and a second absorption image 12 and a first dark field image 11 and a second dark field image 13 by arranging a plurality of gratings and an object T in a first relative position and a second relative position, a step of acquiring a parallel movement amount (x, y) and a rotational movement amount (θz) of the second absorption image 12, and a step of performing a position adjustment of the first dark field image 11 and the second dark field image 13 based on the parallel movement amount (x, y) and the rotational movement amount (θz) of the second absorption image 12.

With this, in the first relative position and the second relative position, even in cases where the acquired first dark field image 11 and second dark field image 13 are different in shape, based on the parallel movement amount (x, y) and the rotational movement amount (θz) of the second absorption image 12 having the same shape of the object T in the first relative position and the second relative position, the position adjustment of the first dark field image 11 and the second dark field image 13 can be performed. As a result, the image position adjustment can be performed even in cases where the shape of the object T imaged differs depending on the positional relationship between the orientation of the grating pattern of the grating and the orientation of the object T.

Second Embodiment

Next, with reference to FIGS. 6 to 10, an X-ray imaging apparatus 200 according to a second embodiment of the present invention will be described. In the second embodiment, a rotation mechanism 30 that relatively rotates the object T in the rotational direction about the axis in the Y-direction is further provided, so that the three-dimensional image can be generated. The same reference numeral is allotted to the same configuration as that of the first embodiment, and the description thereof will be omitted.

Figure 6:
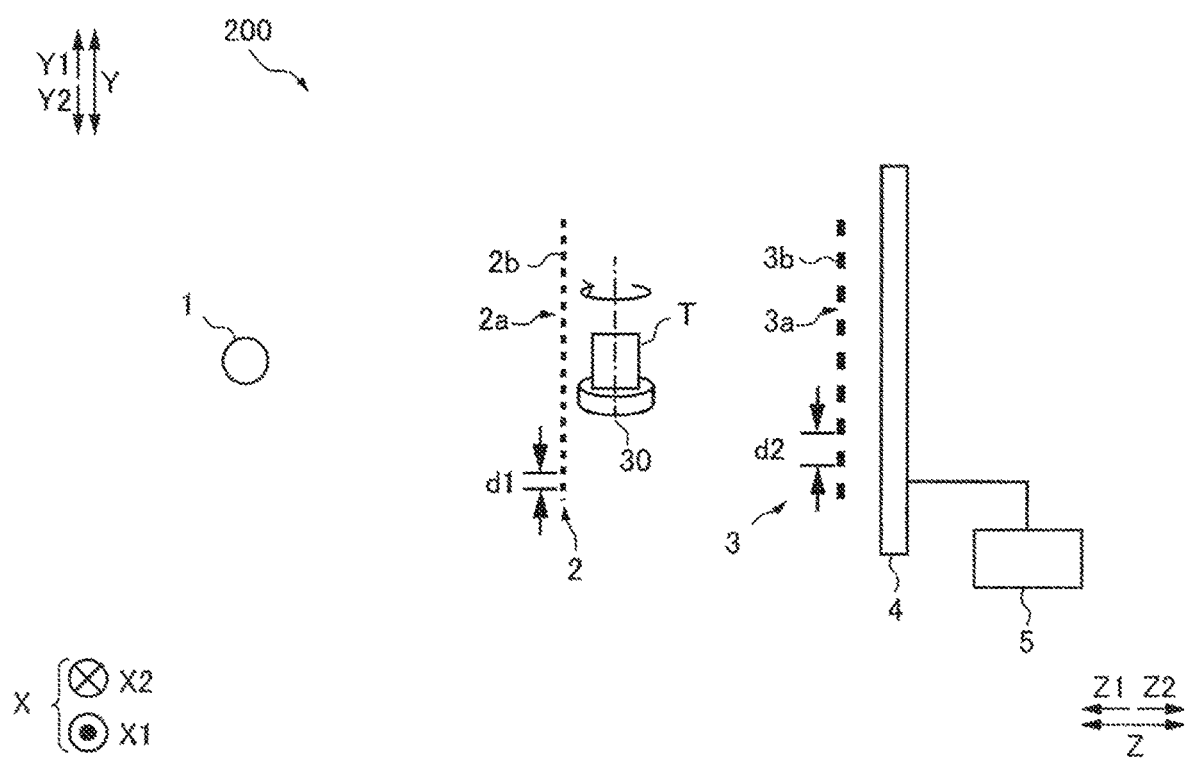
FIG. 6 is a diagram showing an overall structure of an X-ray imaging apparatus according to a second embodiment of the present invention.

As shown in FIG. 6, in the second embodiment, the X-ray imaging apparatus 200 is further provided with a rotation mechanism 30 that relatively rotates the object T in the rotational direction about the axis in the Y-direction.

Figure 7:
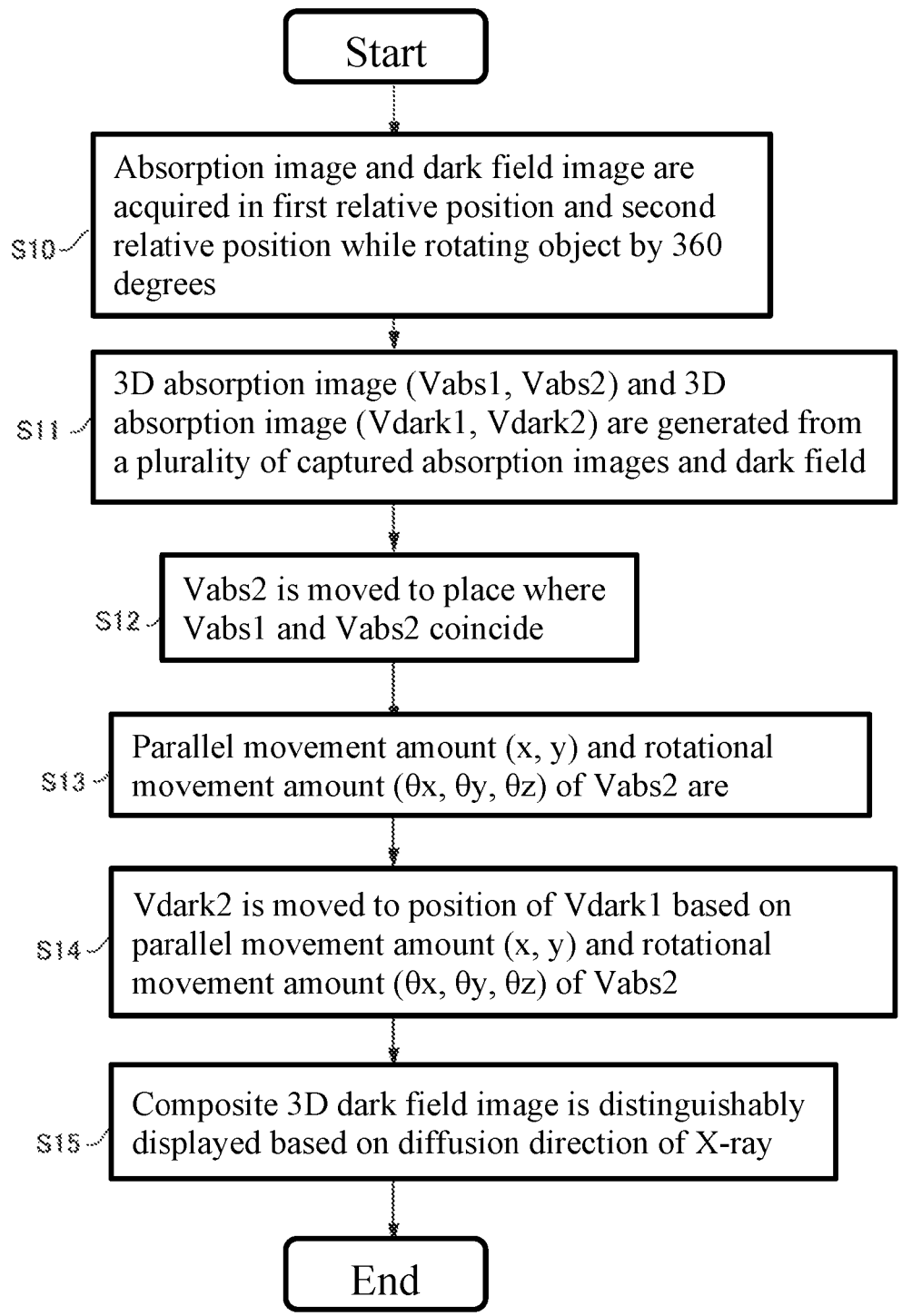
FIG. 7 is a flowchart for explaining a method of composing images by the X-ray imaging apparatus according to the second embodiment of the present invention.
Figure 8A:
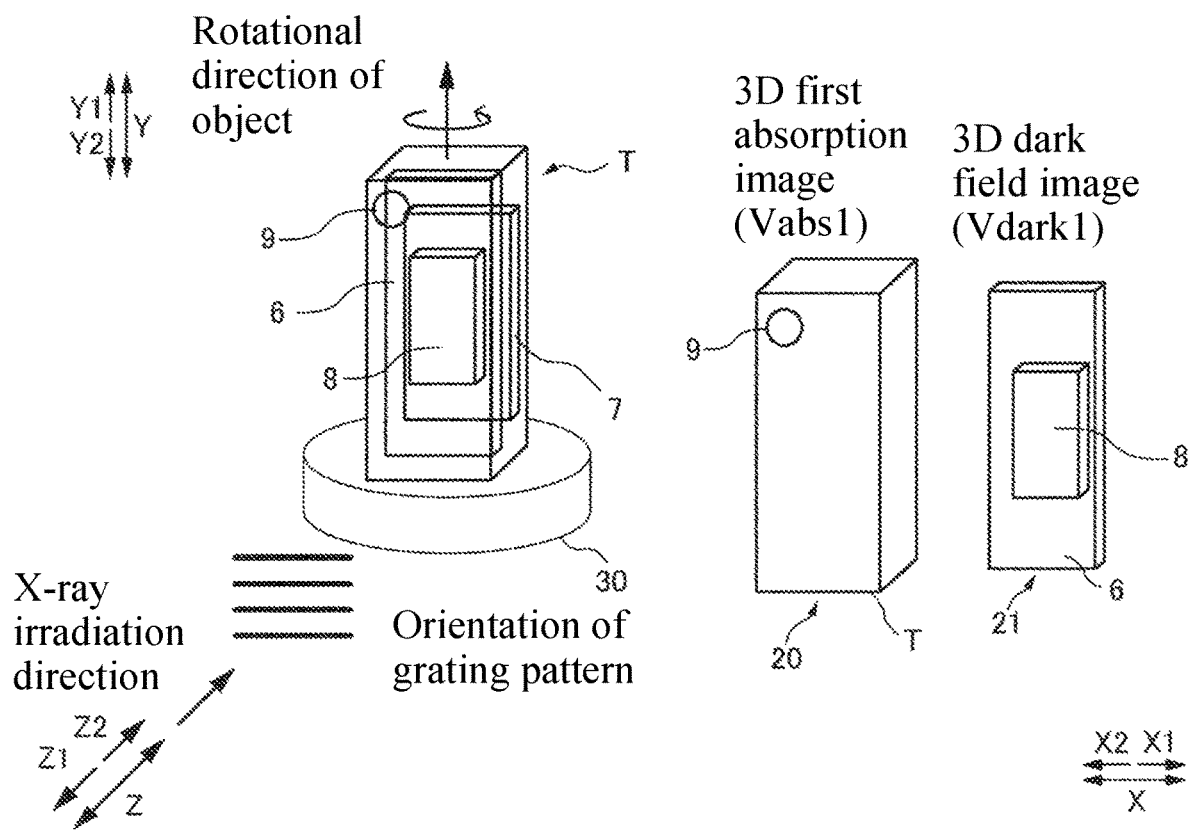
FIG. 8A is a schematic diagram for explaining a first relative position and images to be captured in the first relative position according to the second embodiment of the present invention.
Figure 8B:
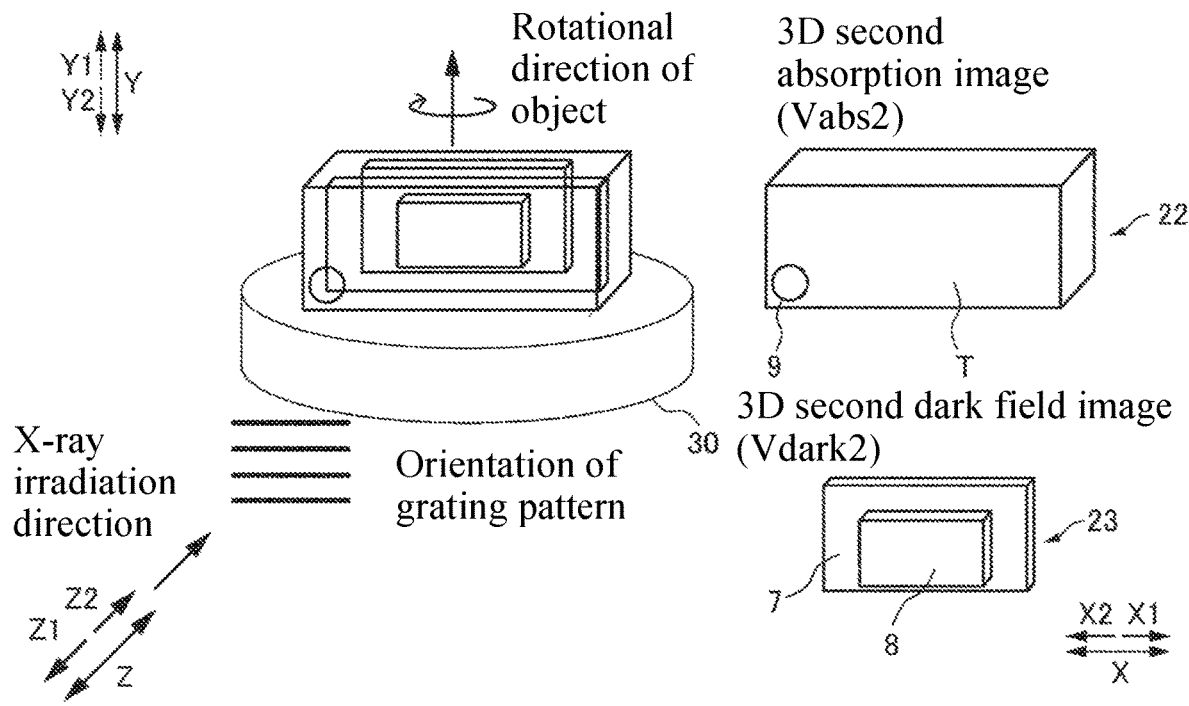
FIG. 8B is a schematic diagram for explaining a second relative position and images to be captured in the second relative position according to the second embodiment of the present invention.

Next, with reference to FIG. 7, the overall flow of the configuration in which the X-ray imaging apparatus 100 according to the second embodiment composes dark field images will be described.

In Step S10, in the six mutually different axial directions, in addition to the first relative position and the second relative position, in each of the third relative position, the fourth relative position, the fifth relative position, and the sixth relative position in which the object T is arranged so that the orientation of the object T differs with respect to the grating pattern of the plurality of gratings, while rotating the object T by 360 degrees, a plurality of first to sixth absorption images and a plurality of first to sixth dark field images are respectively captured at a position of a predetermined rotation angle. The six mutually different axis directions will be described later.

In the second embodiment, since the image processing unit 5 can generate a three-dimensional image, unlike the first embodiment, in addition to the rotational direction about an axis in the Z-direction, the object T may be arranged so as to be inclined in the rotational direction (θx direction) about the axis in X-direction and/or in the rotational direction (θy direction) about the axis in the Y-direction.

Next, in Step S11, the image processing unit 5 generates three-dimensional absorption images and dark field images corresponding to the respective first to sixth relative positions from a plurality of first to sixth absorption images and a plurality of first to sixth dark field images captured in the respective relative positions of the first relative position to the sixth relative position. That is, the image processing unit 5 generates a three-dimensional 3D first absorption image 20 (see FIG. 8A) (hereinafter referred to as "Vabs1") in the first relative position and a three-dimensional 3D second secondary absorption image 22 (see FIG. 8B) (hereinafter referred to as "Vabs2") in the second relative position.

Also in the third to sixth relative positions, in the same manner as described above, 3D third to sixth absorption images (hereinafter referred to as "Vabs3" to "Vabs6") are generated. Further, the image processing unit 5 generates a three-dimensional 3D first dark field image 21 (see FIG. 8A) (hereinafter referred to as "Vdark1") in the first relative position and a three-dimensional 3D second dark field image 23 (see FIG. 8B) (hereinafter referred to as "Vdark1") in the second relative position. Also in the third to sixth relative positions, in the same manner as described above, 3D third to sixth absorption images (hereinafter referred to as "Vdark3" to "Vdark6") are generated.

Vabs1 to Vabs6 are each an example of the "first image" recited in claims. Further, Vdark1 to Vdark6 are each an example of the "second image" recited in claims.

Next, in Step S12, the image processing unit 5 performs the position adjustment of Vabs2 to Vabs1. Further, the position adjustment of Vabs3 to Vabs6 to Vabs1 is performed to generated a 3D composite absorption image 24 (see FIG. 9) in which Vabs1 to Vabs6 are composed.

Next, in Step S13, the image processing unit 5 acquires the movement amount of Vabs2 at the time of composing the 3D composite absorption image 24. The movement amounts to acquire are a parallel movement amount (x, y) and a rotational movement amount (θx, θy, θz). Also as to Vabs3 to Vabs6, in the same manner as described above, the movement amounts are acquired.

Next, in Step S14, the image processing unit 5 performs the position adjustment of Vdark2 to Vdark1 based on the movement amount (parallel movement amount (x, y) and the rotational movement amount (θx, θy, θz)) of Vabs2 acquired in Step S13. Further, as to the Vdark3 to Vdark6, in the same manner as mentioned above, the position adjustment to Vdark1 is performed to generate a 3D composite dark filed image 25 (see FIG. 9).

Next, in Step S15, the image processing unit 5 distinguishably displays regions different in the X-ray diffusion direction in the 3D composite dark field image 25. Note that the 3D composite dark field image 25 is an example of the "composite image" recited in claims.

Next, with reference to FIGS. 8 and 9, a configuration in which the X-ray imaging apparatus 200 according to the second embodiment performs the position adjustment of Vdark1 and Vdark2 based on the movement amount of Vabs2 and generates a 3D composite absorption image 25 will be described. For the sake of simplicity, FIG. 8 and FIG. 9 describe a configuration in which a 3D composite dark filed image 25 is generated using the captured Vabs1, Vabs2, Vdark1, and Vdark2 in the first relative position and the second relative position.

FIG. 8 is a view showing the orientation of the grating pattern and the orientation in which the object T is arranged in the first relative position and the second relative position. In the second embodiment, as shown in FIG. 8, the rotation mechanism 30 is configured to relatively rotate the object T in the rotational direction about the axis in the Y-direction. The other configurations in the first relative position and the second relative position are the same as those in the first embodiment.

Figure 9:
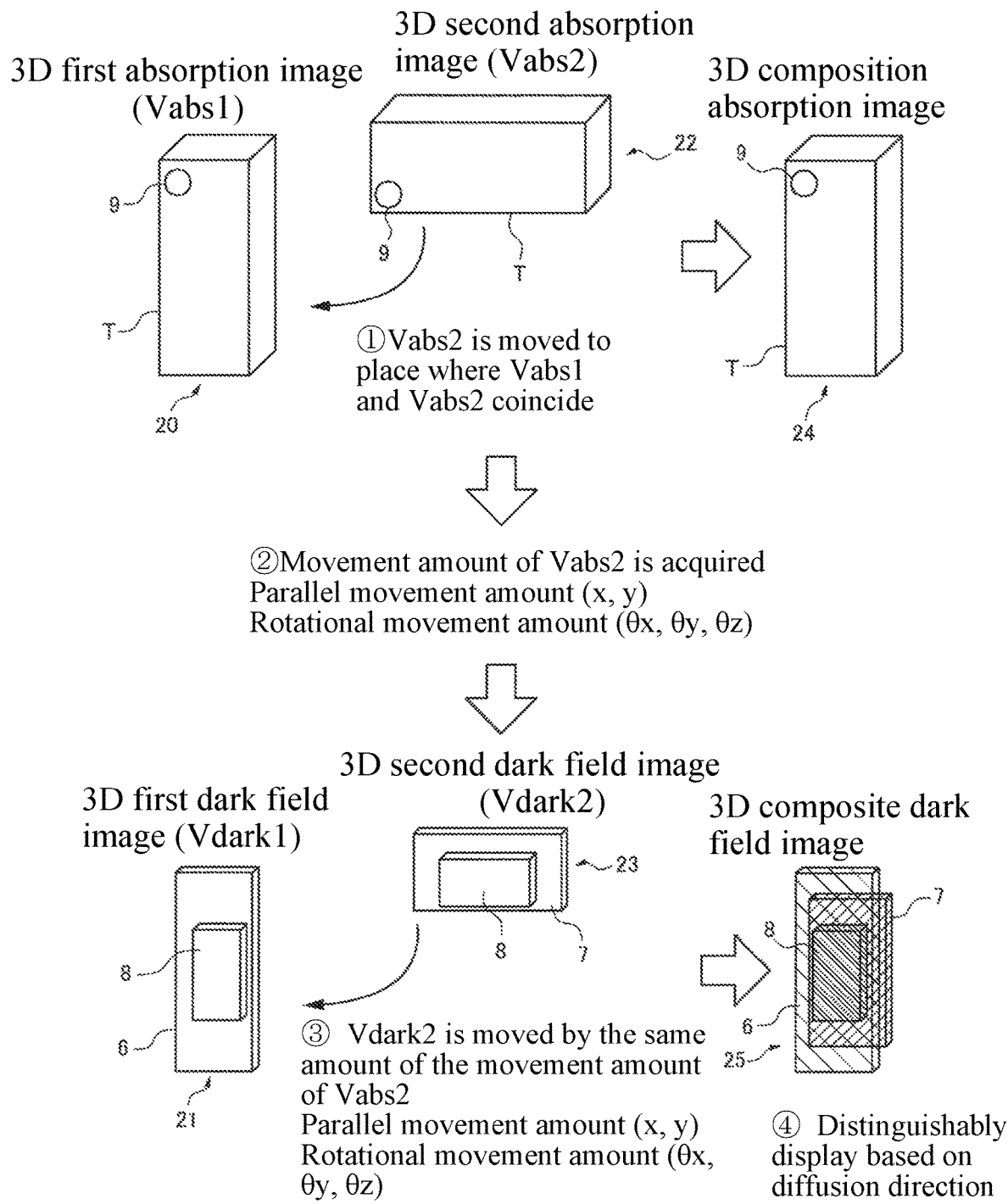
FIG. 9 is a schematic diagram for explaining a method of composing images by the X-ray imaging apparatus according to the second embodiment of the present invention.
Figure 10A:
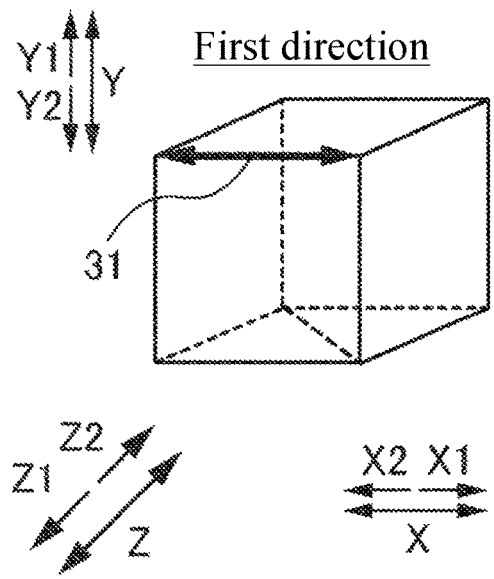
FIG. 10A is a schematic diagram for explaining an orientation in which an object is arranged in a first direction in first to sixth relative positions according to the second embodiment of the present invention.
Figure 10B:
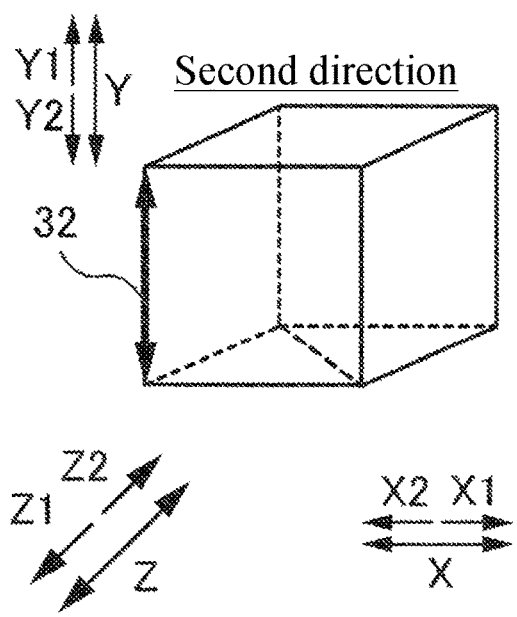
FIG. 10B is a schematic diagram for explaining an orientation in which an object is arranged in a second direction in the first to sixth relative positions according to the second embodiment of the present invention.
Figure 10C:
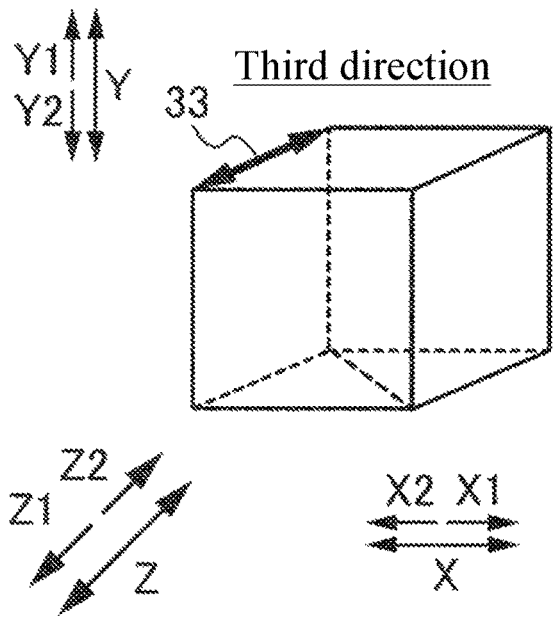
FIG. 10C is a schematic diagram for explaining an orientation in which an object is arranged in a third direction in the first to sixth relative positions according to the second embodiment of the present invention.
Figure 10D:
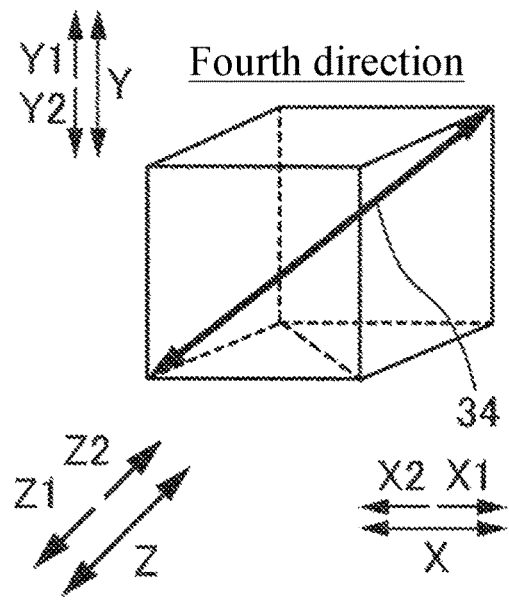
FIG. 10D is a schematic diagram for explaining an orientation in which an object is arranged in a fourth direction in the first to sixth relative positions according to the second embodiment of the present invention.
Figure 10E:
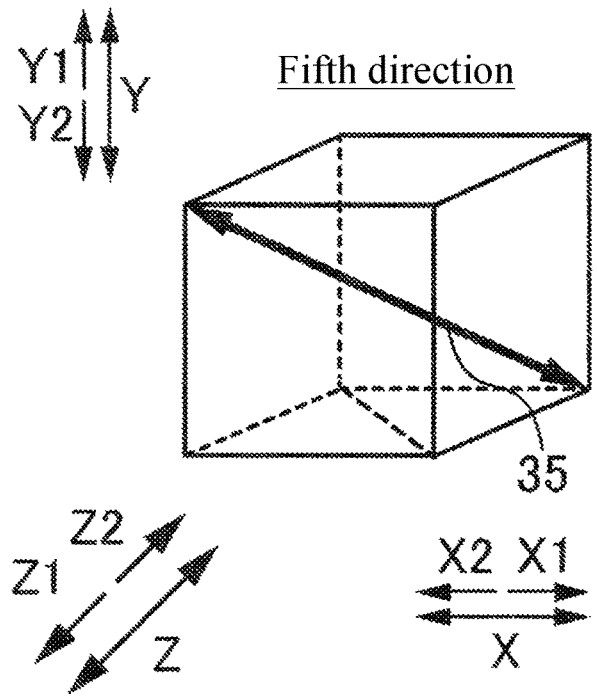
FIG. 10E is a schematic diagram for explaining an orientation in which an object is arranged in a fifth direction in the first to sixth relative positions according to the second embodiment of the present invention.
Figure 10F:
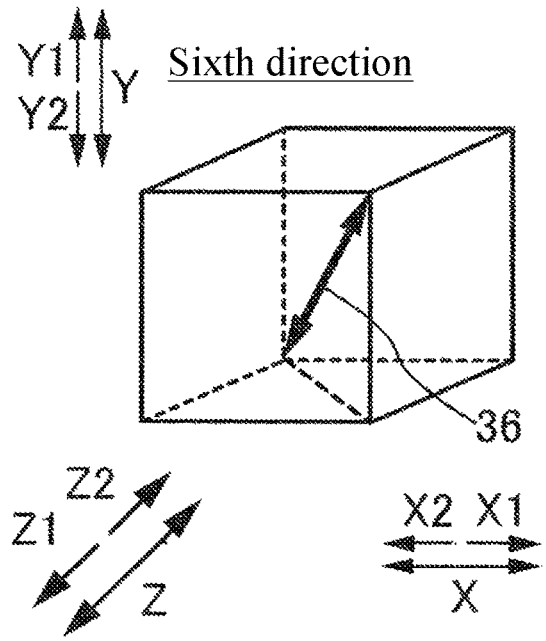
FIG. 10F is a schematic diagram for explaining an orientation in which an object is arranged in a sixth direction in the first to sixth relative positions according to the second embodiment of the present invention.
Figure 10G:
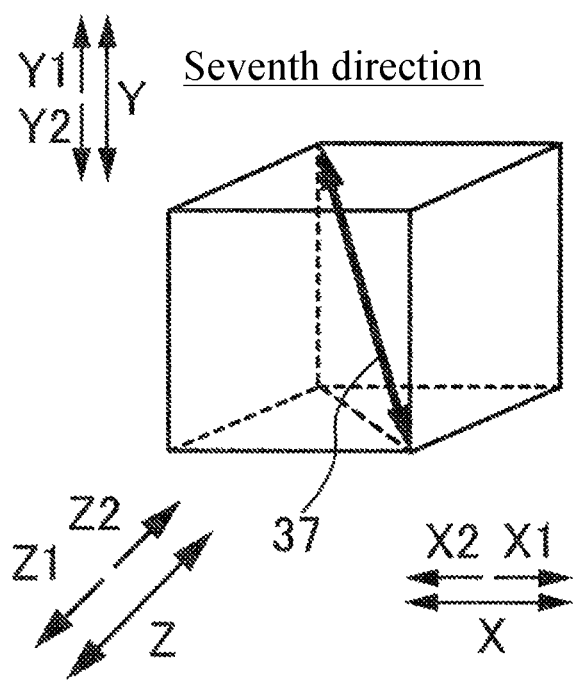
FIG. 10G is a schematic diagram for explaining an orientation in which an object is arranged in a seventh direction in the first to sixth relative positions according to the second embodiment of the present invention.

In the second embodiment, as shown in FIG. 9, it is configured to acquire the movement amount of the second absorption image as the positional difference amount of the object T by performing the position adjustment of Vabs1 in the first relative position and Vabs2 in the second relative position.

The method of the position adjustment is the same as that in the first embodiment. The image processing unit 5 is configured to acquire the parallel movement amount (x, y) and the rotational movement amount (θx, θy, θz) of Vabs2 at the time of the position adjustment and move Vdark2 by the same amount as the acquired parallel movement amount (x, y) and rotational movement amount (θx, θy, θz). Thereafter, the image processing unit 5 composes Vdark1 and Vdark2 in the first relative position and the second relative position to generate a 3D composite dark field image 25.

Further, the image processing unit 5 is configured to distinguishably display regions different in the X-ray diffusion direction in the 3D composite dark field image 25. In the second embodiment, the image processing unit 5 distinguishably displays regions different in the X-ray diffusion direction in the 3D composite dark field image 25 by performing a color display by the value calculated from the luminance values (pixel values) of Vdark1 and Vdark2.

Next, with reference to FIG. 10, the configuration in which the object T is arranged in the first to sixth relative positions in six mutually different axial directions will be described.

FIG. 10 includes FIGS. 10A to 10G for explaining six mutually different axis directions when assuming that the object T is a regular hexahedron. In the second embodiment, relative positions in which the object T is arranged on the rotation mechanism 30 with the first direction 31, the second direction 32, and the third direction 33 shown in FIGS. 10A to 10C oriented in a direction parallel to the Y-direction are defined as a first relative position, a second relative position, and a third relative position, respectively.

The first to third directions are directions parallel to respective axis directions when the object T is assumed to be a regular hexahedron, respectively. That is, the first direction is a direction parallel to the X-direction. Further, the second direction is a direction parallel to the Y-direction. Further, the third direction is a direction parallel to the Z-direction. The first to third directions are directions orthogonal to each other.

Further, in the second embodiment, relative positions in which the object T is arranged on the rotation mechanism 30 with either one of three directions oriented in a direction parallel to the Y-direction among the fourth direction 34, the fifth direction 35, and the sixth direction 36 and the seventh direction 37 shown in FIGS. 10D to 10G. The third to six directions are each one of the four diagonal directions of the regular hexahedron.

In the second embodiment, the image processing unit 5 is configured to generate Vabs1 to Vabs6 and Vdark1 to Vdark6 from a plurality of absorption images and dark field images captured at a position of a predetermined rotation angle while rotating the object T by 360 degrees at each of the first to six relative positions. In FIG. 10, it is assumed that object T is a regular hexahedron, but it is possible to define the first to sixth directions even in cases where the object T is not a regular hexahedron. That is, the first to six directions may be defined by defining a space in the X-direction, Y-direction, and Z-direction in the object T and assuming that a regular hexahedron is present in that space.

In the second embodiment, the image processing unit 5 performs the position adjustment of the Vabs2 to Vabs6 among Vabs1 to Vabs6 generated in the first to sixth relative positions with respect to Vabs1 and acquires the respective movement amounts. Based on the respective acquired movement amounts, the image processing unit 5 performs the position adjustment of Vdark2 to Vdark6 with respect to Vdark1 and generates a 3D composite dark field image 25 by composing Vdark1 to Vdark6.

Other configurations of the second embodiment are the same as those of the first embodiment.

Effects of Second Embodiments

In the second embodiment, the following effects can be obtained.

In the second embodiment, as described above, the X-ray imaging apparatus 200 is further provided with a rotation mechanism 30 that relatively rotates the object T in the rotational direction about the axis in the Y-direction, and the absorption image and the dark field image each contain a three-dimensional image. With this, by performing the position adjustment using Vabs1 and Vabs2, the position adjustment of Vdark1 and Vdark2 can be easily performed. As a result, it becomes possible to grasp in detail the X-ray diffusion direction in the ultrastructure of the inside of the object T. That is, it is possible to acquire an image reflecting the difference in the microscopic structure of the ultrastructure of the inside of the object T or the difference in the shape of the fine structure of the inside of the object.

Further, in the second embodiment, as described above, the image processing unit 5 is configured to generate Vabs1 to Vabs6 and Vdark1 to Vdark6 from the images captured while rotating the object T in each of a third relative position, a fourth relative position, a fifth relative position, and a sixth relative position, which are arranged so that the orientations of the object T with respect to the grating pattern of the plurality of gratings are different from each other in addition to the first relative position and the second relative position, in six mutually different axial directions. With this, for example, it is possible to distinguish the difference in diffusion direction of 45 degrees, 135 degrees, etc. As a result, it is possible to grasp the ultrastructure of the inside of the object in more detail. That is, by capturing images in the first to sixth referential positions, it is possible to grasp an arbitrary diffusion direction of the ultrastructure in the object T.

Other effects of the second embodiment are the same as those of the first embodiment.

Modifications

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the aforementioned embodiments, a phase grating is used as the first grating 2, but the present invention is not limited to this. For example, an absorption grating may be used as the first grating 2. As a result, even in either configuration of the the interferometer and the non-interferometer, it becomes possible to perform X-ray phase-contrast image capturing, which can enhance the degree of freedom in selecting the first grating 2.

Further, in the aforementioned embodiment, an example using an absorption image as the first image is shown, but the present invention is not limited to this. For example, as the first image, an image in which an absorption image, a dark field image and/or a phase differential image are composed may be used.

Further, in the aforementioned embodiment, an example using a dark field image as the second image is shown, but the present invention is not limited to this. For example, as the second image, a phase differential image may be used. In the phase differential image, edges to be emphasized are different depending on the orientation of the object T and the orientation of the grating pattern. In the same manner as in the case of the dark field image, by changing the orientation of the object T and the orientation of the grating pattern, it is possible to grasp the internal structure in more detail. Further, a composite image of an absorption image, a dark field image, and a phase differential image may be used as a second image.

Further, in the aforementioned embodiment, an example is shown in which the composite absorption image 14 and the 3D composite absorption image 24 are generated when obtaining the movement amount of the second absorption image 12 and the 3D second absorption image 22, but the present invention is not limited thereto. The movement amount of the second absorption image 12 and the movement amount of the 3D second absorption image 22 may be obtained without generating the composite absorption image 14 and the 3D composite absorption image 24, respectively.

In the aforementioned embodiment, the object T and the plurality of gratings are arranged in the first relative position and the second relative position by changing the orientation of the object T, but the present invention is not limited thereto. For example, the object T and a plurality of gratings may be arranged in the first relative position and the second relative position by changing the orientation of the grating pattern of a plurality of gratings.

Further, in the above embodiment, an example in which the positional difference amount between the first absorption image 10 (3D first dark field image 21) and the second absorption image 12 (3D second absorption image 22) is obtained by performing the position adjustment is shown, but the present invention is limited to this. Any method can be used as long as a positional difference amount can be acquired.

Further, in the aforementioned embodiment, an example in which a position adjustment of the first absorption image 10 (3D first absorption image 20) and the second absorption image 12 (3D second absorption image 22) by fitting is shown, but the present invention is not limited to this. Any method can be used as long as it can perform the position adjustment of the first absorption image 10 (3D first absorption image 20) and the second absorption image 12 (3D second absorption image 22).

In the aforementioned embodiment, the example in which the object T is not moved in the Z-direction in the first relative position and the second relative position is shown, but the present invention is not limited to this. For example, in the first relative position and the second relative position, the object T may be moved in the Z-direction. In the first relative position and the second relative position, when the object T is moved in the Z-direction, the magnification ratio of the acquired image is different. In that case, the position adjustment of the second dark field image 13 (3D second dark field image 23) can be performed by using, in addition to the position information acquired in the aforementioned embodiment, the magnification ratio acquired by the shape fitting from the first absorption image 10 (3D first absorption image 20) and the second absorption image 12 (3D second absorption image 22) and the position information acquired in the aforementioned embodiment.

Figure 11:
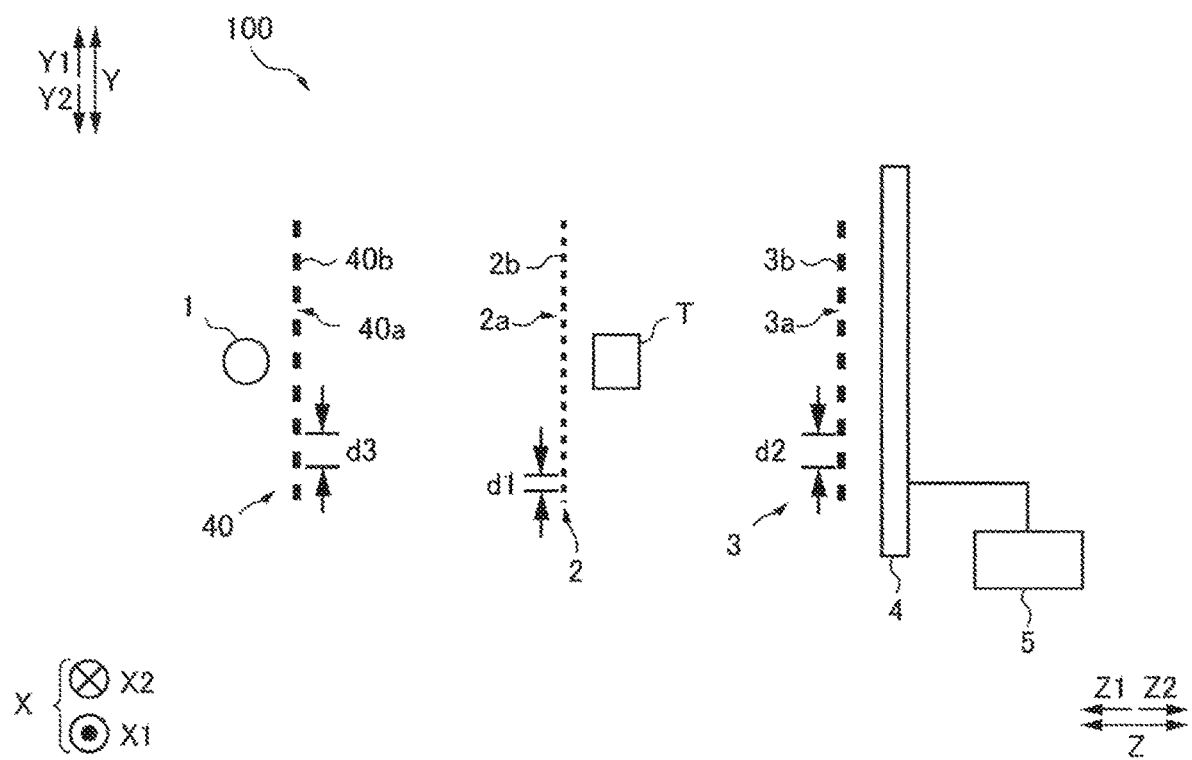
FIG. 11 is a diagram showing an overall structure of an X-ray imaging apparatus according to a first modification of the first embodiment of the present invention.

Further, in the aforementioned embodiment, an example in which the first grating 2 and the second grating 3 are provided as a plurality of gratings is shown, but the present invention is not limited to this. For example, as shown in FIG. 11, the third grating 40 may be provided between the X-ray source 1 and the first grating 2. The third grating 40 is provided with a plurality of slits 40a and X-ray absorptions 40b arranged in the Y-direction at a predetermined period (pitch) d3. The slit 40a and the X-ray absorption portion 40b are each configured to extend in the X-direction. Further, the third grating 40 is arranged between the X-ray source 1 and the first grating 2 and is configured to be irradiated by the X-ray from the X-ray source 1. The third grating 40 is configured to use the X-ray that has passed through each slit 40a as a line light source corresponding to the position of the each slits 40a. With this, the third grating 40 can enhance the coherence of the X-ray emitted from the X-ray source 1.

With this configuration, even in cases where a high-power X-ray source with small coherence of the X-ray source 1 is used, the coherence of the X-ray source can be increased by the third grating 40, so that the the degree of freedom of selection of an X-ray source can be improved.

In the second embodiment, an example in which the rotation mechanism 30 relatively rotates the object T is shown, but the present invention is not limited thereto. For example, the rotation mechanism 30 may be configured to rotate the imaging system including the X-ray source 1, a plurality of gratings, and the detectors 4.

Further, in the second embodiment, the first to sixth relative positions in the six mutually different axial directions are determined by changing the orientation of the object T arranged on the rotation mechanism 30, but the present invention is not limited thereto. For example, the first to sixth relative positions may be determined by tilting the rotation mechanism 30 without changing the orientation of the object T. Further, the first to third relative positions may be determined by tilting the rotation mechanism 30 in three mutually different directions. Further, the first to fourth relative positions may be determined by tilting the rotation mechanism 30 in four mutually different directions. Further, the first to five relative positions may be determined by tilting the rotation mechanism 30 in five mutually different directions.

Further, in the second embodiment, an example in which image capturing is performed by arranging the object T in the first to sixth position is shown, but the present invention is not limited thereto. For example, a configuration may be adopted in which the object T is arranged in any two positions out of the first to sixth relative positions to capture images. Also, it is possible to adopt a configuration in which the object T is arranged in 2 to 5 positions out of the first to sixth relative positions to capture images, or a configuration in which the object T is arranged in more than 7 positions may be used.

The invention claimed is:

1. An X-ray imaging apparatus comprising:
an X-ray source;
a detector configured to detect an X-ray irradiated from the X-ray source;
a plurality of gratings arranged between the X-ray source and the detector, the plurality of gratings including a first grating to which the X-ray is irradiated from the X-ray source and a second grating to which the X-ray that has passed through the first grating is irradiated; and
an image processing unit configured to generate a first image including an absorption image and a second image including an image other than the absorption image captured in the same arrangement as the first image from an intensity distribution of the X-ray detected by the detector,
wherein the image processing unit is configured to perform a position adjustment of the second image in the first relative position and the second image in the second relative position based on a positional difference amount of an object between the first image in the first relative position and the first image in the second relative position among images captured by arranging the plurality of gratings and the object in the first relative position and the second relative position in two mutually different axial directions.

2. The X-ray imaging apparatus as recited in claim 1, wherein
the image processing unit is configured to acquire a movement amount of the first image as the positional difference amount of the object by performing a position adjustment of the first image in the first relative position and the first image in the second relative position.

3. The X-ray imaging apparatus as recited in claim 2, wherein
the image processing unit is configured to perform the position adjustment of the first image by performing fitting from shape information of the object of the first image in the first relative position and the second relative position, acquire the movement amount of the first image at the time of the position adjustment by the fitting, and move the second image by the same amount as the acquired movement amount.

4. The X-ray imaging apparatus as recited in claim 1, wherein the second image is either one of a dark field image and a phase differential image.

5. The X-ray imaging apparatus as recited in claim 1, wherein
the first relative position is a relative position in which the plurality of gratings and the object are arranged such that the object faces in a predetermined direction with respect to the grating pattern of the plurality of gratings, and
the second relative position is a relative position in which the plurality of gratings and the object are arranged such that an orientation of the object with respect to the grating pattern of the plurality of gratings differs from the first relative position.

6. The X-ray imaging apparatus as recited in claim 1, further comprising a rotation mechanism configured to relatively rotate either one of the object and an imaging system including the X-ray source, the detector, and the plurality of gratings in a rotational direction about an axis in a vertical direction orthogonal to an optical axis direction of the X-ray, wherein the first image and the second image each include a three-dimensional image.

7. The X-ray imaging apparatus as recited in claim 6, wherein
the image processing unit is configured to generate the first image and the second image from images captured while rotating the object or the imaging system in each of a third relative position, a fourth relative position, a fifth relative position, and a sixth relative position, which are arranged so that the orientation of the object with respect to the grating pattern of the plurality of gratings differs, in addition to the first relative position and the second relative position, in each of six mutually different axial directions.

8. The X-ray imaging apparatus as recited in claim 1, wherein
the image processing unit is configured to compose the second image in the first relative position and the second image in the second relative position and display regions different in a diffusion direction of the X-ray in a composite image.

9. The X-ray imaging apparatus as recited in claim 1, wherein
the image processing unit is configured to perform the position adjustment of the first image based on an X-ray high absorbency marker provided on the object.

10. A method of composing an X-ray imaging image, comprising:
a step of capturing a first image including an absorption image and a second image including an image other than the absorption image with a plurality of gratings and an object arranged in a first relative position and a second relative position in two mutually different axial directions;
a step of acquiring a movement amount from the first image in the first relative position to the first image in the second relative position; and
a step of performing a position adjustment of the second image based on the movement amount of the first image.

* * * * *